(12) United States Patent
Kim et al.

(10) Patent No.: US 11,890,332 B2
(45) Date of Patent: Feb. 6, 2024

(54) DUAL-SCALE POROUS SILICA PARTICLE-BASED COMPOSITION FOR PREVENTING OR TREATING CANCER

(71) Applicant: Research & Business Foundation Sungkyunkwan University, Suwon-si (KR)

(72) Inventors: Jae Yun Kim, Suwon-si (KR); Nguyen Thanh Loc, Suwon-si (KR)

(73) Assignee: Research & Business Foundation Sungkyunkwan University, Suwon-si (KR)

(*) Notice: Subject to any disclaimer, the term of this patent is extended or adjusted under 35 U.S.C. 154(b) by 295 days.

(21) Appl. No.: 17/073,656

(22) Filed: Oct. 19, 2020

(65) Prior Publication Data
US 2021/0113675 A1 Apr. 22, 2021

(30) Foreign Application Priority Data
Oct. 17, 2019 (KR) .......... 10-2019-0129468
Feb. 24, 2020 (KR) .......... 10-2020-0022569

(51) Int. Cl.
A61K 39/00 (2006.01)
A61K 9/14 (2006.01)
A61K 47/69 (2017.01)
A61K 47/02 (2006.01)
A61K 9/51 (2006.01)

(52) U.S. Cl.
CPC .......... *A61K 39/0011* (2013.01); *A61K 9/143* (2013.01); *A61K 9/5115* (2013.01); *A61K 47/02* (2013.01); *A61K 47/6923* (2017.08); A61K 2039/5152 (2013.01); A61K 2039/5154 (2013.01); A61K 2039/55555 (2013.01)

(58) Field of Classification Search
None
See application file for complete search history.

(56) References Cited

PUBLICATIONS

Cha, Bong Geun, Ji Hoon Jeong, and Jaeyun Kim. "Extra-large pore mesoporous silica nanoparticles enabling co-delivery of high amounts of protein antigen and toll-like receptor 9 agonist for enhanced cancer vaccine efficacy." ACS central science 4.4 (Mar. 28, 2018): 484-492 and S1-S5. (Year: 2018).*
Kim, Jaeyun, et al. "Injectable, spontaneously assembling, inorganic scaffolds modulate immune cells in vivo and increase vaccine efficacy." Nature biotechnology 33.1 (2015): 64-72 and S1-S16. (Year: 2015).*
Lei, Chenghong, et al. "Local release of highly loaded antibodies from functionalized nanoporous support for cancer immunotherapy." Journal of the American Chemical Society 132.20 (2010): 6906-6907 and S1-S5. (Year: 2010).*
Song, Botao, et al. "Dual Drug Release from Electrospun Poly (lactic-co-glycolic acid)/Mesoporous Silica Nanoparticles Composite Mats with Distinct Release Profiles." Acta Biomaterialia, vol. 8, May 2012, (7 pages in English).
Kim, Jaeyun, et al. "Injectable, Spontaneously Assembling, Inorganic Scaffolds Modulate Immune Cells in Vivo and Increase Vaccine Efficacy." Nature Biotechnology, Jan. 2015, vol. 33, (25 pages in English).
Xu, Chun, et al. "Rod-Like Mesoporous Silica Nanoparticles with Rough Surfaces for Enhanced Cellular Delivery." Journal of Materials Chemistry B, vol. 2, Nov. 2013, (4 pages in English).
Zhao, Huan, et al. "The Application of Nanoparticle-Based Drug Delivery Systems in Checkpoint Blockade Cancer Immunotherapy." Journal of Immunology Research Sep. 2018 (13 pages in English).
Nguyen, Thanh Loc, et al. "Mesoporous Silica as a Versatile Platform for Cancer Immunotherapy." Advanced Materials vol. 31, Nov. 2018 (17 pages in English).
Korean Office Action dated Sep. 7, 2021 in counterpart Korean Patent Application No. 10-2020-0022569 (8 pages in English and 7 pages in Korean).
Banchereau, J. et al. "Dendritic cells and the control of immunity" Nature 392, 245-252, Mar. 19, 1998 (8 pages in English).
Banchereau J. et al. "Immunobiology of dendritic cells" Annu Rev Immunol. Apr. 2000 (48 Pages in English).
Singh, A. et al. "Hydrogels and Scaffolds for Immunomodulation" Adv. Mater. Aug. 25, 2014 (12 Pages in English).
Munn, D. et al. "Immune suppressive mechanisms in the tumor microenvironment" Curr. Opin. Immunol. Nov. 21, 2015 (6 Pages in English).
Zhu, G. et al. "Efficient Nanovaccine Delivery in Cancer Immunotherapy" ACS Nano. Mar. 9, 2017 (6 Pages in English).
El-Khoueiry, A.B. et al. "Nivolumab in patients with advanced hepatocellular carcinoma (CheckMate 040): an open-label, non-comparative, phase 1/2 dose escalation and expansion trial" Lancet. Apr. 20, 2017 (11 Pages in English).
Milling, L. et al. "Delivering safer immunotherapies for cancer" Adv. Drug Deliv. Rev. May 22, 2017 (23 Pages in English).

* cited by examiner

Primary Examiner — Bethany P Barham
Assistant Examiner — Peter Anthopolos
(74) Attorney, Agent, or Firm — NSIP Law

(57) ABSTRACT

The present invention relates to a dual-scale porous silica particle-based pharmaceutical composition for preventing or treating cancer, which includes porous silica nanoparticles and porous silica microparticles. The pharmaceutical composition of the present invention promotes the generation of a larger amount of antigen-specific, cytotoxic T cells against cancer than a mesoporous silica nanoparticle (MSN) vaccine, and exhibits increased anti-tumor efficacy compared with a mesoporous silica microrod (MSR) vaccine.

13 Claims, 42 Drawing Sheets

FIG. 4B

| Vaccine | Dose of vaccine components | | | | |
|---|---|---|---|---|---|
| | MSN | MSR | GM-CSF | OVA | CpG-ODNs |
| MSN vaccine | 111 µg | | | 100 µg | 10 µg |
| MSR vaccine | | 5 mg | 1 µg | 100 µg | 10 µg |
| MSR-MSN vaccine | 111 µg | 5 mg | 1 µg | 100 µg | 10 µg |

FIG. 5A

| Vaccine | Relative dose of components | | |
|---|---|---|---|
| | MSN | OVA | CpG-ODNs |
| V1 | 1X | 1X | 1X |
| V2 | 3X | 1X | 1X |
| V3 | 3X | 1X | 3X |
| V4 | 3X | 3X | 3X |

DUAL-SCALE POROUS SILICA PARTICLE-BASED COMPOSITION FOR PREVENTING OR TREATING CANCER

CROSS REFERENCE TO RELATED APPLICATIONS

This application claims the benefit under 35 USC § 119(a) of Korean Patent Application No. 10-2019-0129468 and Korean Patent Application No. 10-2020-0022569, filed on Oct. 17, 2019 and Feb. 24, 2020, respectively, in the Korean Intellectual Property Office, the entire disclosures of which are incorporated herein by reference for all purposes.

TECHNICAL FIELD

The present invention relates to a porous silica nanoparticle and a pharmaceutical composition for preventing or treating cancer, which is based on dual-scale porous silica particles including porous silica nanoparticles and microparticles.

BACKGROUND ART

Cancer immunotherapy, which uses a patient's immune system to treat cancer, is carried out clinically, and is having positive effects [1]. Cancer generates an immunosuppressive tumor microenvironment (TME) through various mechanisms such as PD1/PD-ligand inhibitory pathway, myeloid-derived suppressor cell, regulatory T cells, indoleamine 2,3-dioxygenase and counter-regulation, which suppress the immunological function of host T cells [2]. To induce cancer antigen-specific adaptive immune responses, such as cytotoxic T lymphocytes (CTLs) in the TME, cancer vaccines utilize dendritic cells (DCs), which are the most potent antigen-presenting cells (APCs). DCs are considered to be a bridge between innate immunity and adaptive immunity, and capable of sampling information of antigens released in tumor and presenting it to naive $CD8^+$ and $CD4^+$ T cells in draining lymph nodes (dLNs) via major histocompatibility complex (MHC) class I (MHC-I) and MHC class II (MHC-II) [3, 4]. Accordingly, the efficient antigen-specific activation of host DCs caused by delivering immunological signals such as an antigen and an adjuvant is an essential process for developing cancer vaccines inducing cancer-specific and potent adaptive immunity.

Recently, various material-based cancer vaccines have received considerable attention due to their potential to control the immune system with well-designed biomaterials [5]. Nanoparticles simultaneously carrying antigens and adjuvants are emerging as a prominent tool for cancer vaccines [6]. Nanoparticle-based vaccines are expected to be delivered to dLNs where immature DCs are present, internalized into peripheral DCs around an injection site, followed by returning to the dLNs. However, after intradermal or subcutaneous administration, the efficiency of delivering nanoparticles to dLNs is relatively low because of diffusion of nanoparticles around local injection site and a limited number of peripheral DCs. For these reasons, passive dLN trafficking of nanocarriers is dominant Particularly, large 100 nm nanoparticles have lower possibility of reaching and being localized in dLNs [7]. Therefore, if targeting of DCs or lymph nodes is not accurately controlled, it is difficult to achieve sufficient therapeutic results.

PRIOR ART DOCUMENTS

Non-Patent Documents (Non-patent document 1) A. B. El-Khoueiry et al., Lancet. 389 (2017) 2492-2502

(Non-patent document 2) D. H. Munn et al., Curr. Opin. Immunol. 39 (2016) 1-6

(Non-patent document 3) J. Banchereau et al., Annu. Rev. Immunol. (2000) 767-811

(Non-patent document 4) J. Banchereau et al., Nature. 392 (1998) 245-252

(Non-patent document 5) A. Singh et al., Adv. Mater. 26 (2014) 6530-6541

(Non-patent document 6) G. Zhu et al., ACS Nano. 11 (2017) 2387-2392

(Non-patent document 7) L. Milling et al., Adv. Drug Deliv. Rev. 114 (2017) 79-101

DISCLOSURE

Technical Problem

Therefore, the inventors found that the combination of nanoparticles carrying antigens and adjuvants; and a three-dimensional (3D) macroporous scaffold system that recruits (attracts) DCs; can significantly enhance the efficacy of cancer vaccines by recruiting large amounts of DCs in a 3D scaffold space, and then simultaneously providing the antigens and adjuvants, which are carried by the nanoparticles, to the DCs, and thus the present invention was completed.

Accordingly, the present invention is directed to providing a dual-scale porous silica particle-based pharmaceutical composition for preventing or treating cancer.

The present invention is also directed to providing a dual-scale porous silica particle-based cancer vaccine pharmaceutical composition.

The present invention is also directed to providing a pharmaceutical composition for cancer immunotherapy.

However, technical problems to be solved in the present invention are not limited to the above-described problems, and other problems which are not described herein will be fully understood by those of ordinary skill in the art from the following descriptions.

Technical Solution

To attain the purposes of the present invention, the present invention provides a dual-scale porous silica particle-based pharmaceutical composition for preventing or treating cancer, which includes: (a) an antigen- and adjuvant-loaded porous silica nanoparticle; and (b) a porous silica microparticle carrying a chemoattractant attracting DCs.

In addition, the present invention provides a dual-scale porous silica particle-based cancer vaccine pharmaceutical composition, which includes: (a) an antigen- and adjuvant-loaded porous silica nanoparticle; and (b) a porous silica microparticle carrying a chemoattractant attracting DCs.

Further, the present invention provides a pharmaceutical composition for cancer immunotherapy, which includes the pharmaceutical composition and an immune checkpoint inhibitor.

Moreover, the present invention provides a method of preventing or treating cancer, which includes administering the pharmaceutical composition to a subject in need thereof.

Furthermore, the present invention provides a method of cancer immunotherapy, the method comprising administering the pharmaceutical composition and an immune checkpoint inhibitor a subject in need thereof.

Furthermore, the present invention provides a use of the pharmaceutical composition for preventing, alleviating or treating cancer.

In addition, the present invention provides a use of the pharmaceutical composition for preparing a formulation for preventing or treating cancer.

In one embodiment of the present invention, the porous silica microparticles form a 3D construct with a micro-sized space between the particles by self-assembly in the body, and the porous silica nanoparticles may be located in the space of the 3D construct, but the location is not limited thereto.

In another embodiment of the present invention, the porous silica nanoparticles may be adsorbed onto the surface of porous silica microparticles, but the present invention is not limited thereto.

In still another embodiment of the present invention, immature DCs may be recruited into the micro-sized space, and the porous silica nanoparticles may be internalized into the recruited DCs, but the present invention is not limited thereto.

In yet another embodiment of the present invention, the immature DCs in which the uptake of the porous silica nanoparticles occurs may undergo maturation and migrate to lymph nodes, but the present invention is not limited thereto.

In yet another embodiment of the present invention, the porous silica nanoparticles may be mesoporous silica nanoparticles, but the present invention is not limited thereto.

In yet another embodiment of the present invention, the porous silica nanoparticles may be 30 to 250-nm nanoparticles having a pore size of 3 to 30 nm, but the present invention is not limited thereto.

In yet another embodiment of the present invention, the porous silica nanoparticles may be modified to have a charged surface, but the present invention is not limited thereto.

In yet another embodiment of the present invention, the porous silica nanoparticles whose surface is modified to be charged may be amine-modified nanoparticles, or charged polymer-adsorbed nanoparticles, but the present invention is not limited thereto.

In yet another embodiment of the present invention, the antigens or adjuvants may be loaded in a manner selected from the group consisting of loaded in pores of the porous silica nanoparticles, loaded by electrostatic attraction and a combination thereof, but the present invention is not limited thereto.

In yet another embodiment of the present invention, the porous silica microparticles may be rod-like, polygonal or spherical shaped, but the present invention is not limited thereto.

In yet another embodiment of the present invention, the porous silica microparticles may be a mesoporous silica microrod, but the present invention is not limited thereto.

In yet another embodiment of the present invention, the porous silica microparticles may have a length of 30 to 120 µm and a width of 5 to 30 µm, but the present invention is not limited thereto.

In yet another embodiment of the present invention, the antigen may be a cancer antigen, but the present invention is not limited thereto.

In yet another embodiment of the present invention, the chemoattractant may be selected from the group consisting of a granulocyte macrophage-colony stimulating factor (GM-CSF), chemokine (C-C motif) ligand 21 (CCL-21), chemokine (C-C motif) ligand 19 (CCL-19), a FMS-like tyrosine kinase 3 (Flt-3) ligand and a combination thereof, but the present invention is not limited thereto.

In yet another embodiment of the present invention, the composition may have an increased anticancer effect according to the increase in content of porous silica nanoparticles or adjuvants loaded in the porous silica nanoparticles, but the present invention is not limited thereto.

In yet another embodiment of the present invention, the composition may further comprise an immune checkpoint inhibitor, but the present invention is not limited thereto.

In yet another embodiment of the present invention, the immune checkpoint inhibitor may be an antibody specifically binding to cytotoxic T-lymphocyte-associated protein 4 (CTLA-4), programmed cell death protein 1 (PD-1) or programmed death-ligand 1 (PD-L1), but the present invention is not limited thereto.

Advantageous Effects

A pharmaceutical composition and cancer vaccine of the present invention further promote the generation of large amounts of antigen-specific, cytotoxic T cells against cancer, compared to a mesoporous silica nanoparticle (MSN) vaccine, and exhibit increased antitumor efficacy compared to a mesoporous silica microrod (MSR) vaccine. In addition, since the pharmaceutical composition of the present invention exhibits a higher anticancer effect in combination with conventional cancer immunotherapy, it has promise as a cancer vaccine platform that can be used in combination with an immune checkpoint blockade (ICB) antibody.

DESCRIPTION OF DRAWINGS

FIG. 2 shows that an MSR-MSN vaccine assists the uptake of MSNs by recruited DCs and DC migration to dLNs over time:

Specifically.

"Ns" indicates insignificant, *P<0.05, P<0.01, *P<0.001, and ****P<0.0001.

Figure 3A:
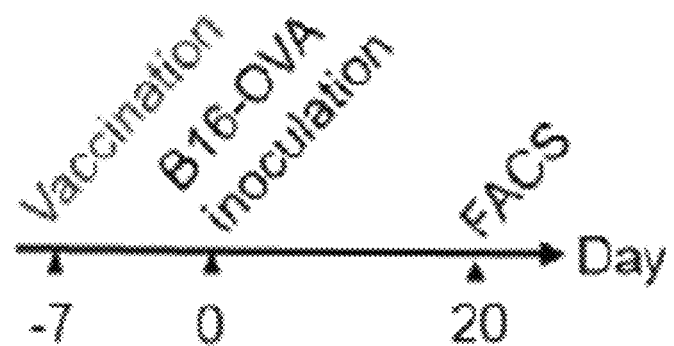
Figure 3B:
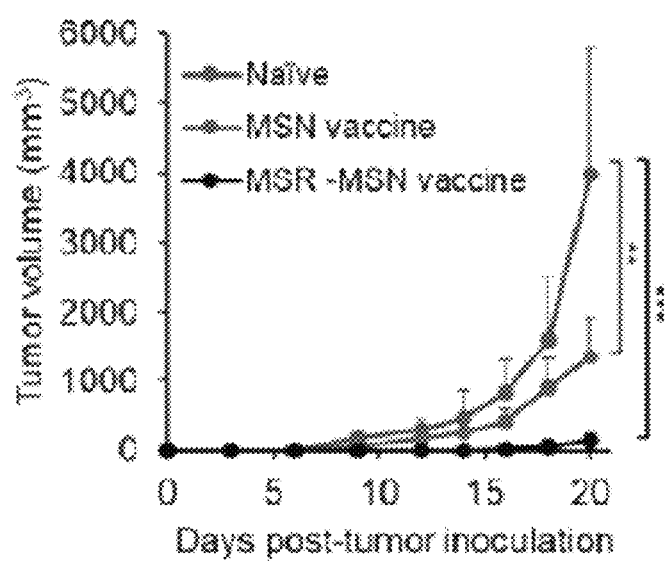
Figure 3C:
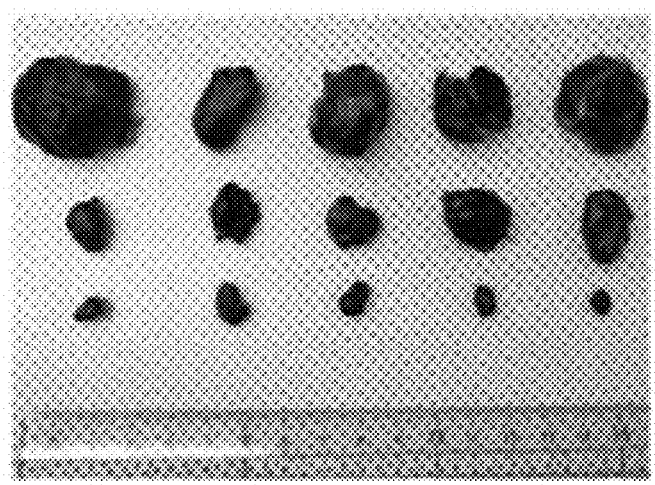
Figure 3D:
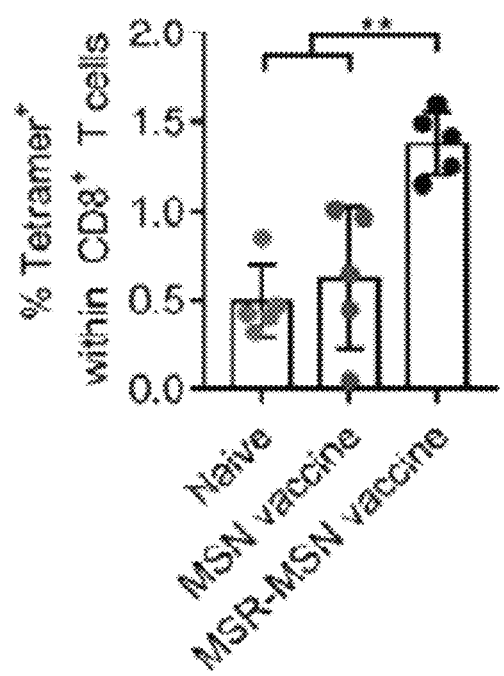
Figure 3E:
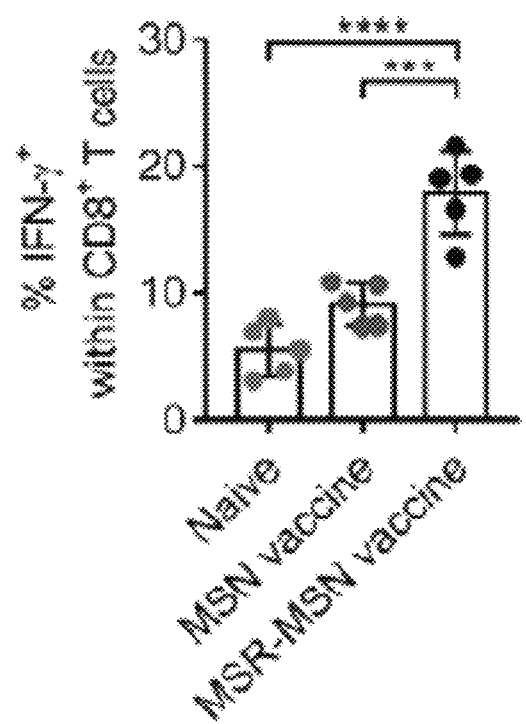
Figure 3F:
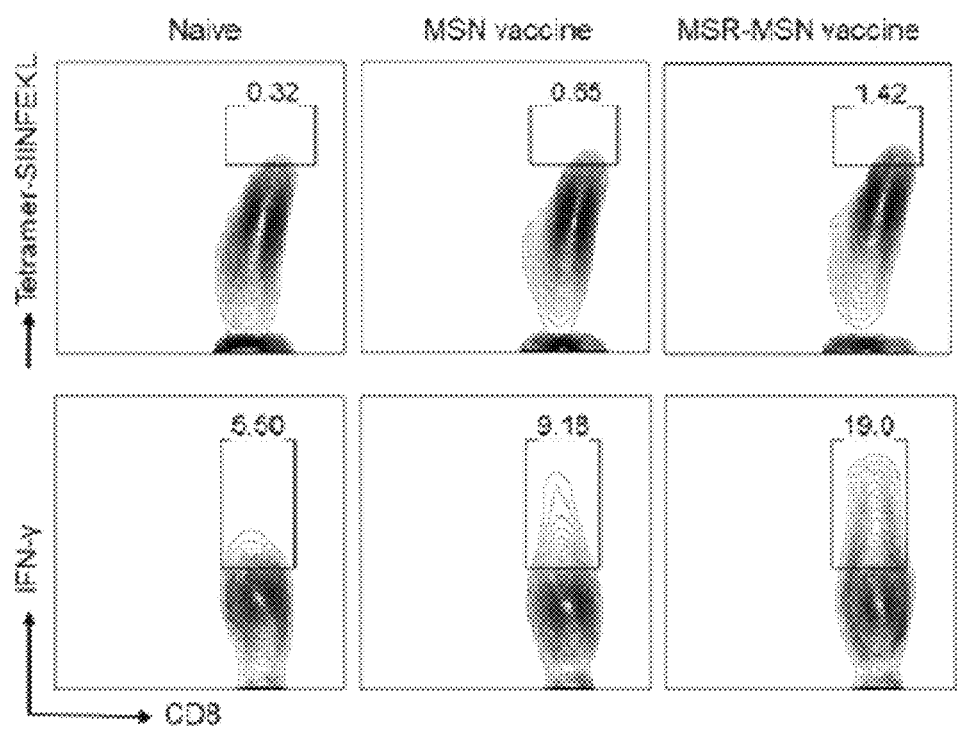

FIG. 3 shows that the MSR-MSN vaccine induces a significant antigen-specific CD8$^+$ T cell response:

Specifically, FIG. 3A shows a prophylactic test schedule, and specifically, 5×10$^5$ B16-OVA cells are inoculated into a mouse flank on day 7 after immunization with the MSN vaccine, the MSR-MSN vaccine or no vaccine (naive) (n=5);

FIG. 3B shows an average tumor growth graph;

FIG. 3C is an image of tumors excised from all mice on day 20 (tumors on the first line, second line and third line are derived from naive mice, MSN vaccine-vaccinated mice and MSR-MSN vaccine-vaccinated mice, respectively);

FIGS. 3D and 3E show percentages of tetramer$^+$ and IFN-γ$^+$ in the CD8$^+$ T cell population in splenocytes, respectively; and FIG. 3F shows a set of flow cytometry dot plots corresponding to FIGS. 3D and 3E, wherein data in FIGS. 3B, 3D and 3E are expressed as the mean±SD, and analyzed by one-way ANOVA. *P<0.001, **P<0.0001.

Figure 4A:
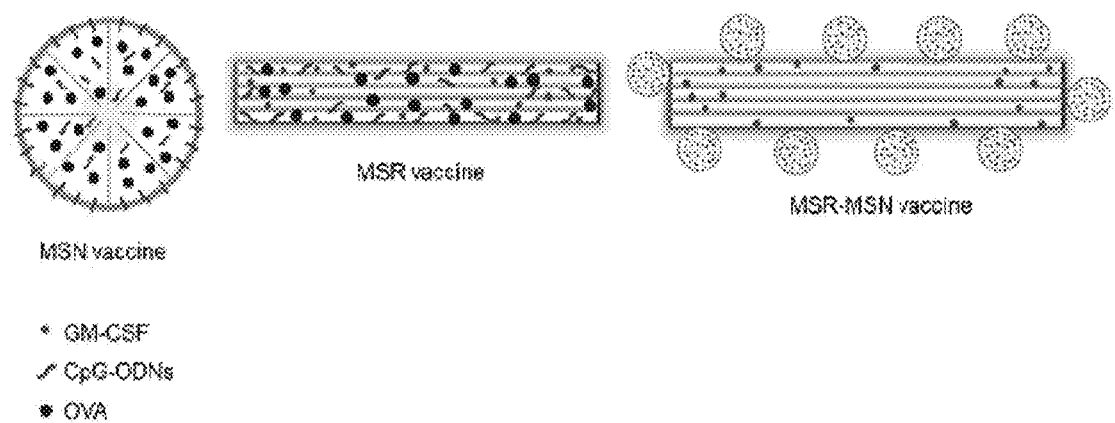
Figure 4C:
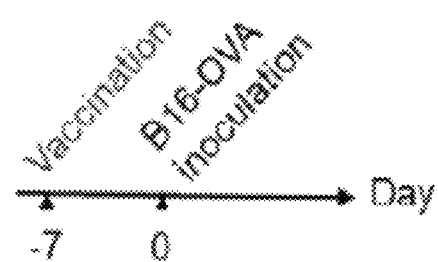
Figure 4D:
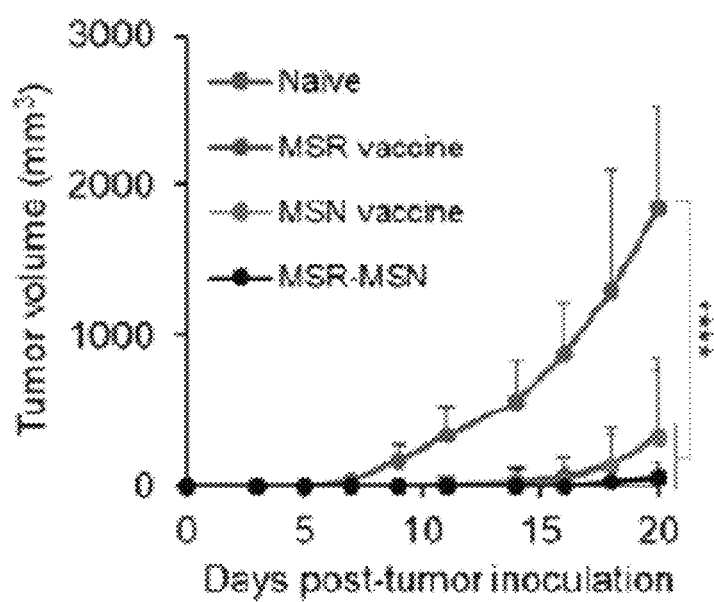
Figure 4E:
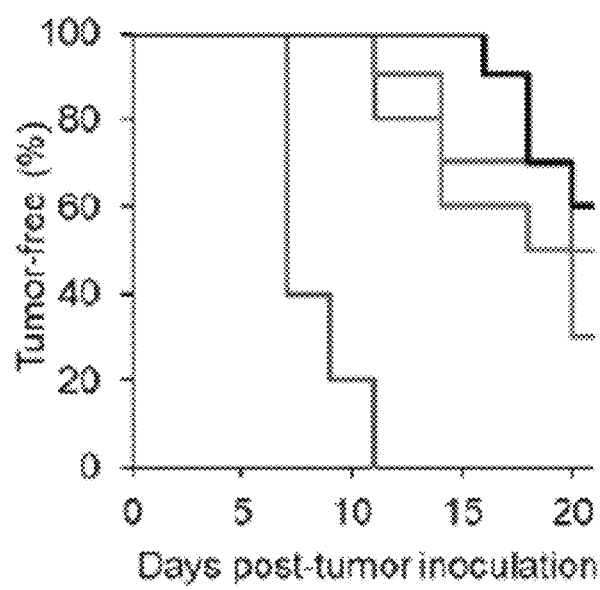
Figure 4F:
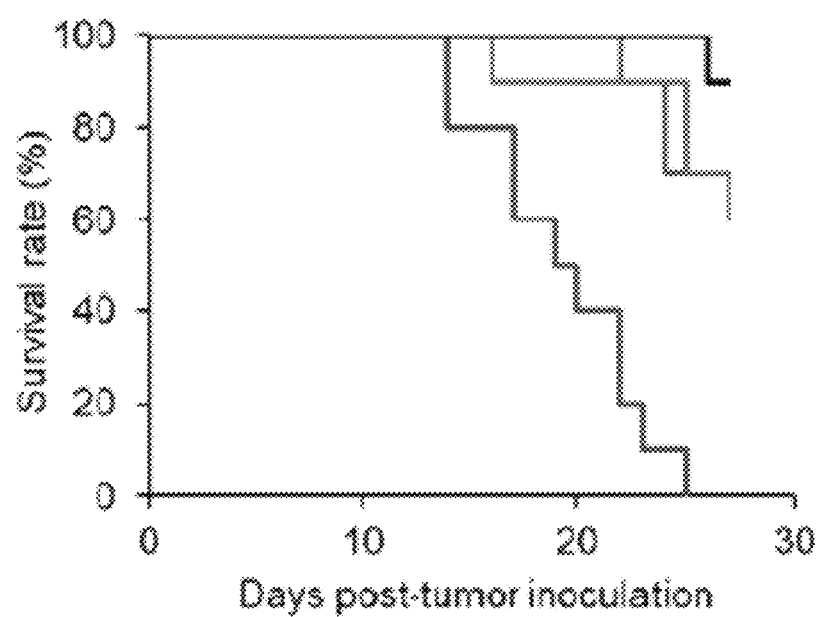
Figure 4G:
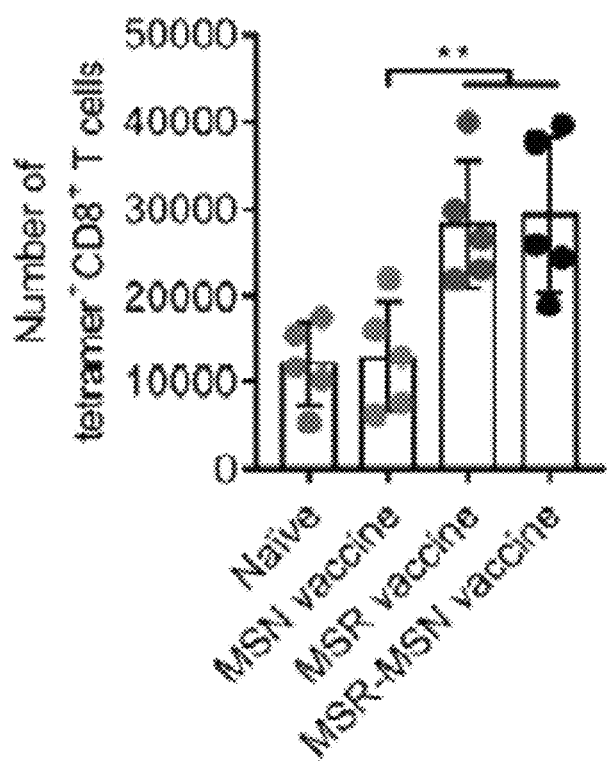
Figure 4H:
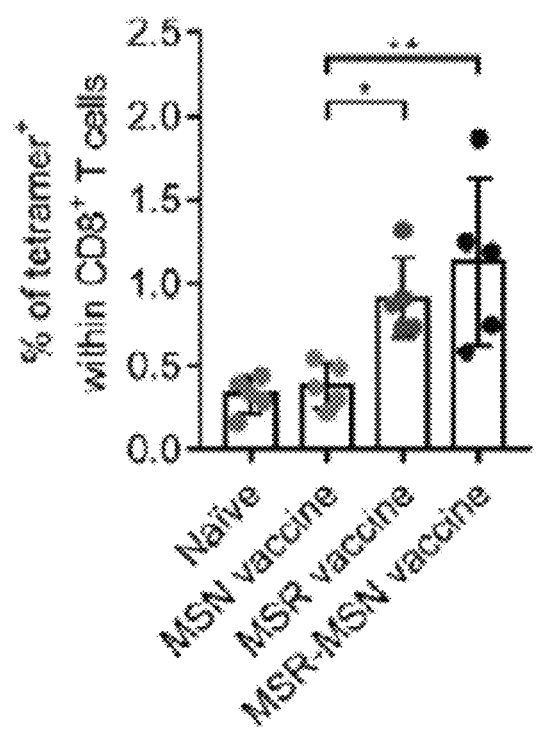

FIG. 4 shows that the MSR-MSN vaccine more effectively suppresses tumor growth than MSN and MSR vaccines:

Specifically, FIG. 4A is a set of schematic diagrams of MSN, MSR and MSR-MSN vaccines;

FIG. 4B shows the doses of vaccine components;

FIG. 4C shows that C57BL/6 mice are vaccinated with the MSN vaccine, MSR vaccine, MSR-MSN vaccine and no vaccine (naive) 7 days before tumor inoculation (n=10);

FIGS. 4D, 4E and 4F show average tumor volumes, the percentage of tumor-free mice and the survival rate of mice under the above-described immunization conditions, respectively. C57BL/6 mice are vaccinated with the MSN vaccine, the MSR vaccine, the MSR-MSN vaccine and no vaccine (naive) 7 days before the isolation of splenocytes (n=5);

FIG. 4G shows the number of tetramer$^+$CD8$^+$ T cells in the spleen;

FIG. 4H shows the percentage of CD8$^+$ T cells expressing tetramers; and

Figure 4I:
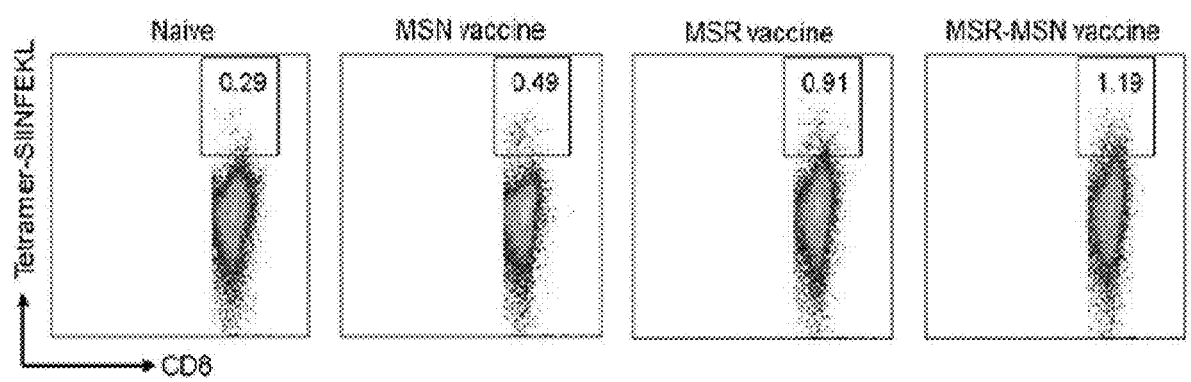

FIG. 4I shows representative dot plots in the spleen, wherein data of FIGS. 4D, 4G and 4H are expressed as the mean±SD, and analyzed by one-way ANOVA. *P<0.05, P<0.01, **P<0.0001.

Figure 5B:
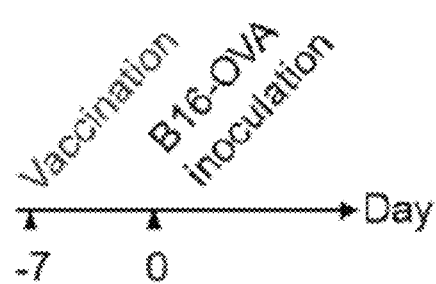
Figure 5C:
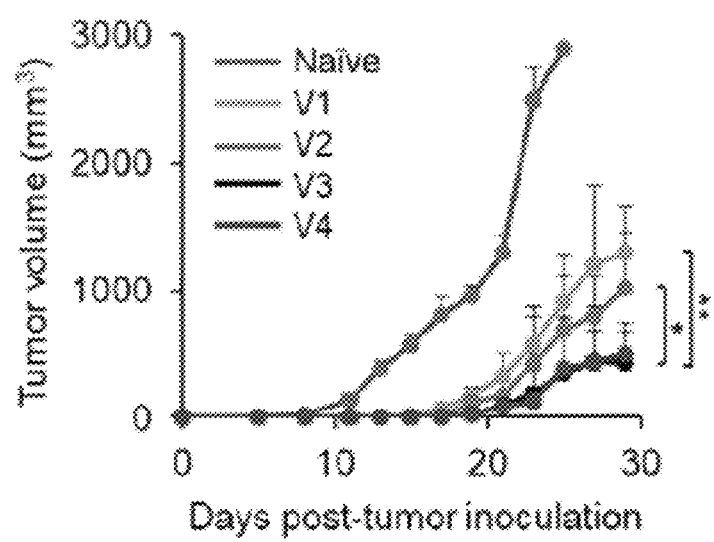

FIG. 5 shows the optimization of a vaccine formulation:

Specifically, FIG. 5A shows the relative dose of each component in different vaccine formulations used in experiments;

FIG. 5B shows that C57BL/6 mice are vaccinated with the MSR-MSN vaccine 7 days before B16-OVA tumor inoculation (n=8);

FIG. 5C shows the average tumor volumes after tumor inoculation; and

Figure 5D:
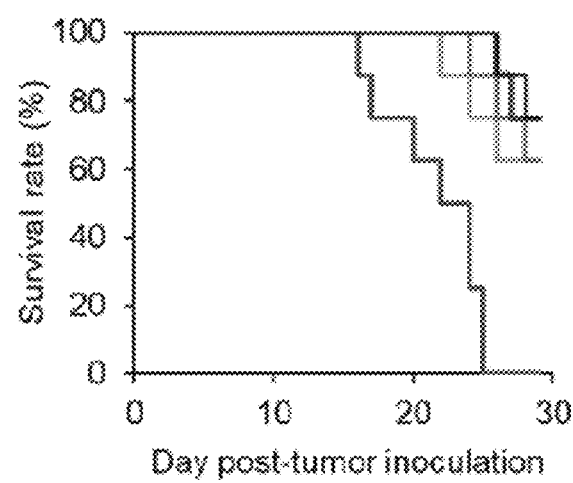

FIG. 5D shows the animal survival rate after tumor inoculation, wherein data of FIG. 5C are expressed as the mean±SD, and analyzed by one-way ANOVA. *P<0.05, **P<0.01.

Figure 6A:
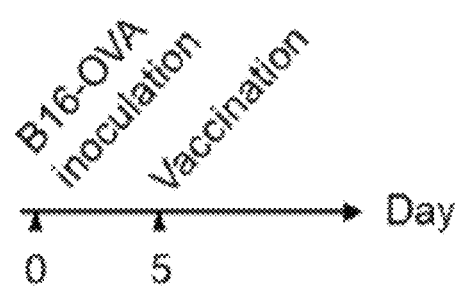
Figure 6B:
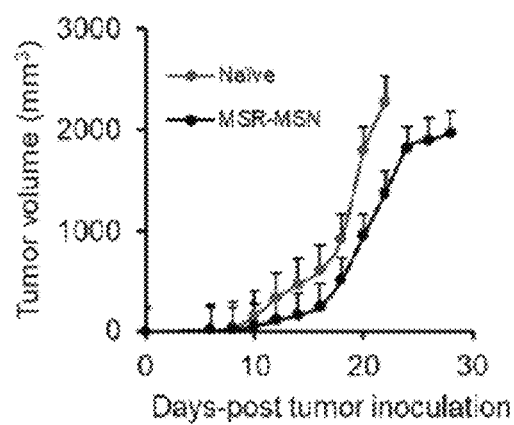
Figure 6C:
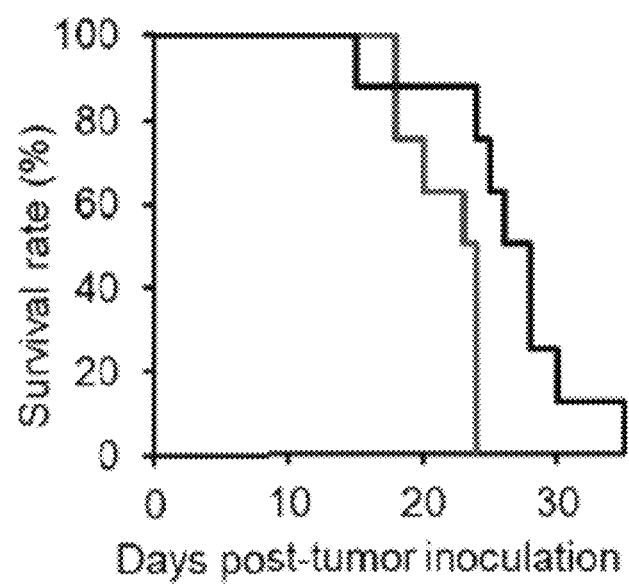
Figure 6D:
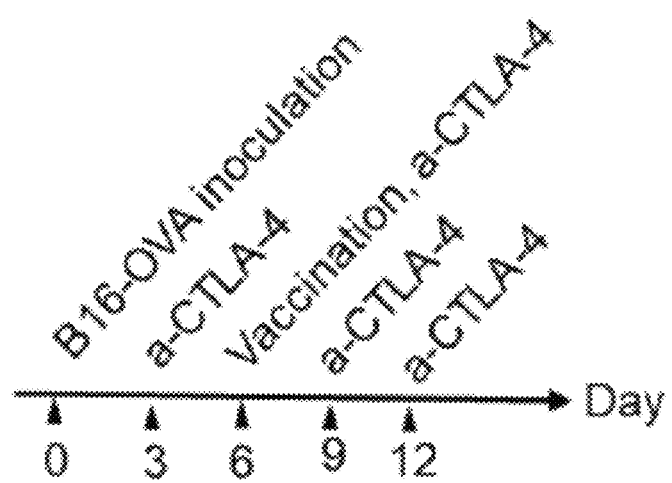
Figure 6E:
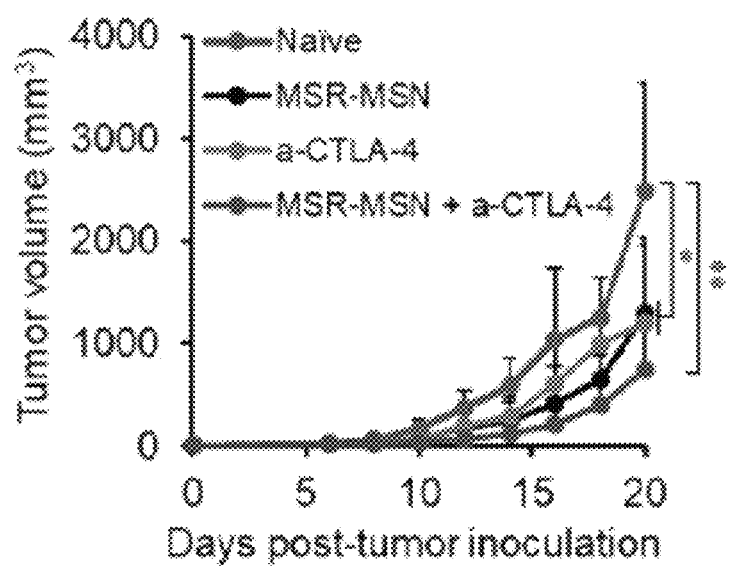

FIG. 6 is a set of diagrams for a therapeutic cancer vaccine experiment by a combination of an established MSR-MSN vaccine for treating melanoma with a-CTLA-4 antibody:

Specifically, FIG. 6A shows that B16-OVA tumor-bearing mice are vaccinated with the MSR-MSN vaccine on day 5 after tumor inoculation (n=8);

FIG. 6B shows the tumor volume after tumor inoculation;

FIG. 6C shows the survival rate after tumor inoculation;

FIG. 6D shows that B16-OVA tumor-bearing mice are vaccinated with the MSR-MSN vaccine (MSR-MSN), an anti-CTLA-4 antibody (a-CTLA4) or a combination of a-CTLA4 with the MSR-MSN vaccine (MSR-MSN+a-CTLA-4) 6 days after tumor inoculation. The a-CTLA is intraperitoneally injected every third day for 3 to 12 days (n=8);

FIG. 6E shows the average tumor volume of animals after tumor inoculation; and

Figure 6F:
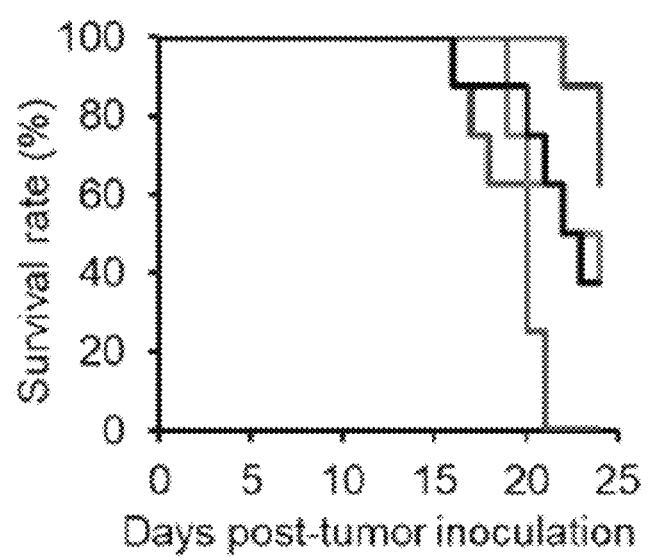

FIG. 6F shows the survival rate of animals after tumor inoculation; wherein data of FIG. 6B are expressed as the mean±SD. Data of FIG. 6E is expressed as the mean±SD and analyzed by one-way ANOVA. *P<0.05, **P<0.01.

Figure 7:
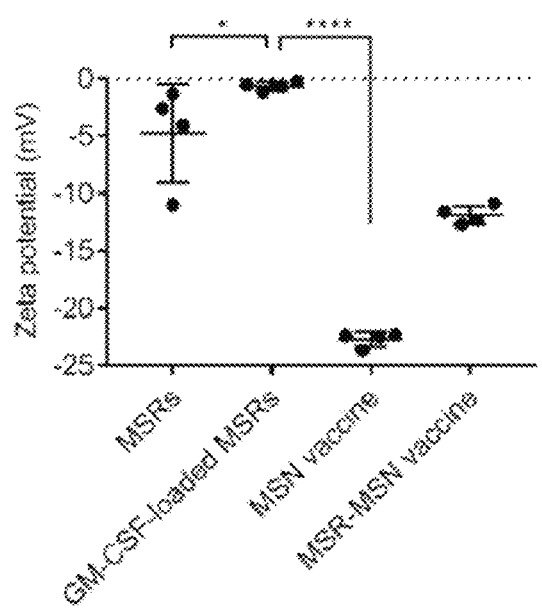

FIG. 7 is a graph of the zeta potential of the MSR vaccine, a GM-CSF-loaded MSR vaccine, the MSN vaccine and the MSR-MSN vaccine. Data are expressed as the mean±SD, and analyzed by one-way ANOVA. *P<0.05, ****P<0.0001.

Figure 8:
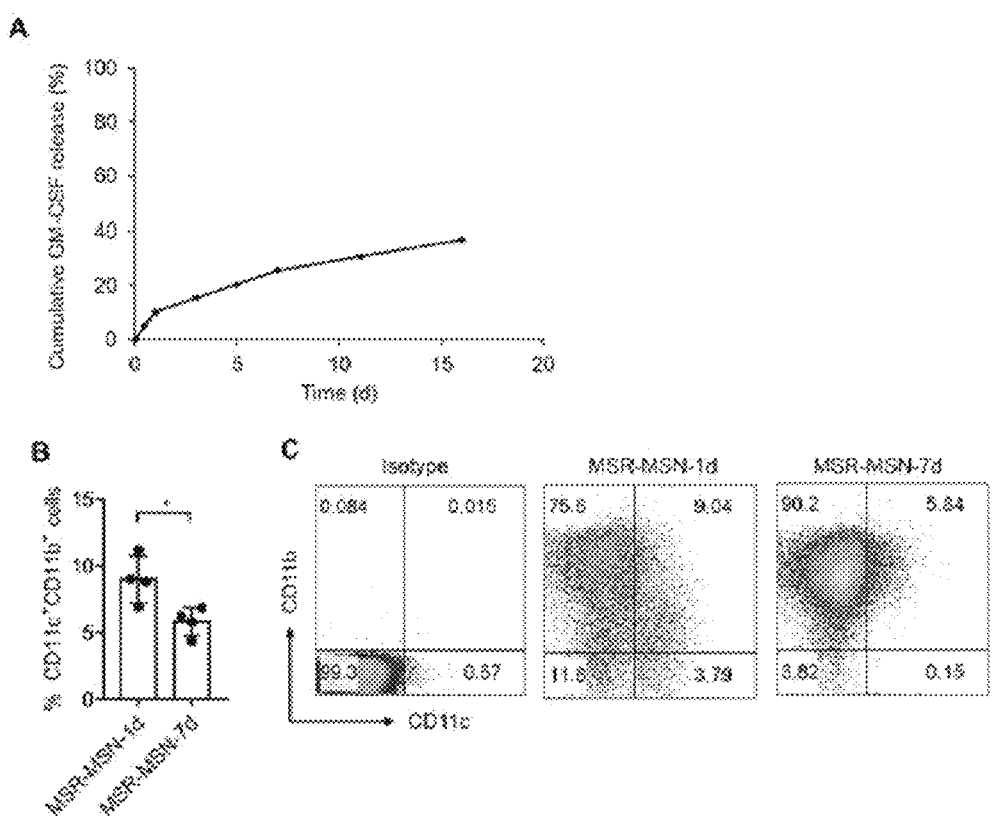

FIG. 8 shows that the MSR-MSN vaccine recruited host DCs into a scaffold over time through continuous release of GM-CSF. A shows in vitro release of GM-CSF from an MSR scaffold (n=4). C57BL/6 mice are injected with MSR-MSN vaccines one day (MSR-MSN-1d) and 7 days (MSR-MSN-7d) before the recruited host immune cells are retrieved, respectively (n=4). B and C show the percentage of CD11c$^+$CD11b$^+$ cells and representative flow cytometry dot plots, respectively. Data of A and B are expressed as the mean±SD, and analyzed by a two-tailed Student t-test. *P<0.05.

Figure 9:
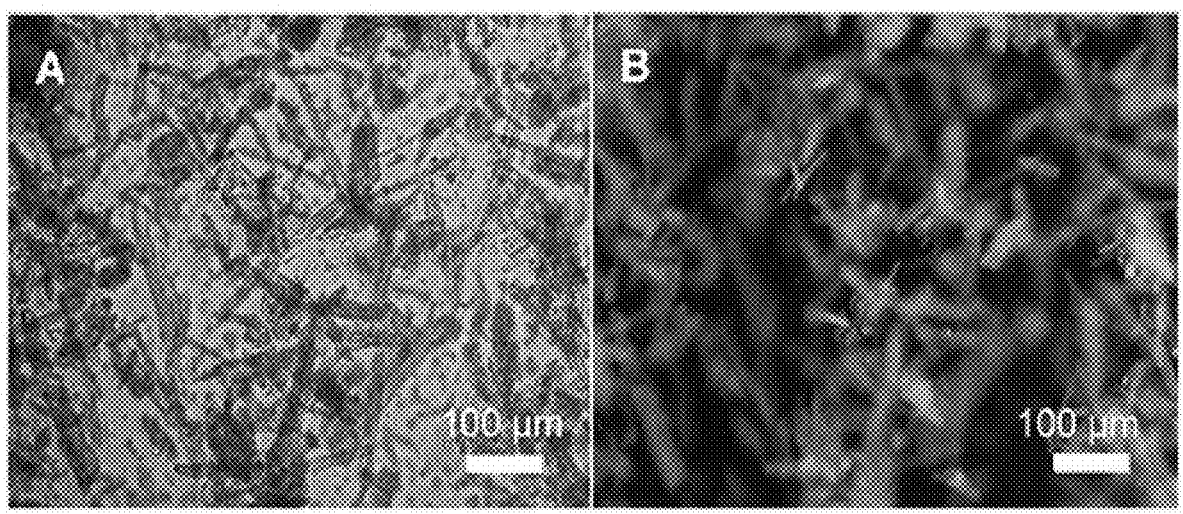

FIG. 9 shows an optical microscope image (A) and a fluorescence microscope image (B) of MSR-RITC-MSN dual-scale particles after cell filtration on day 7.

Figure 10:
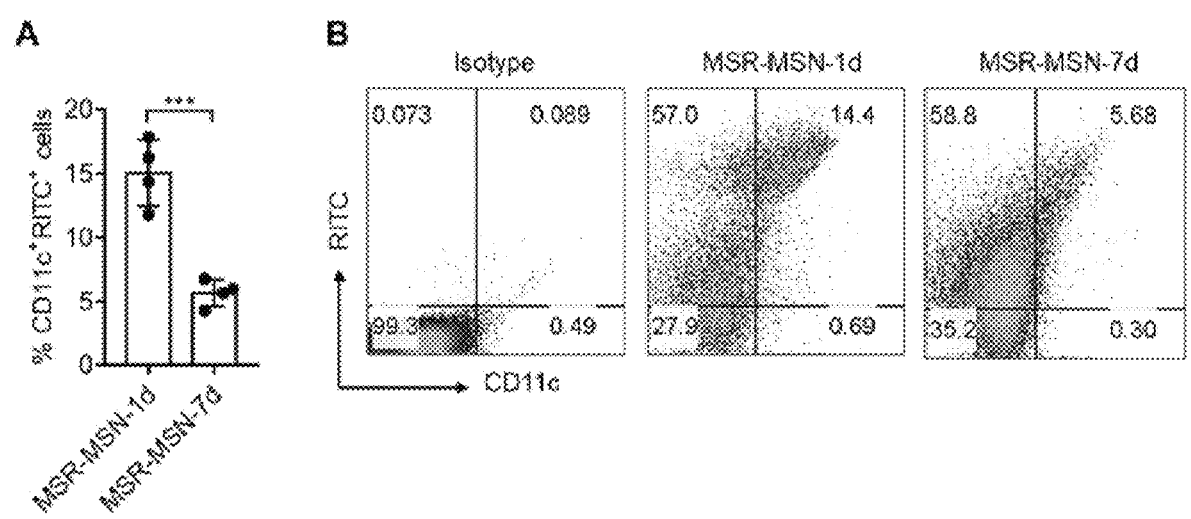

FIG. 10 shows the percentage of RITC-MSN-internalized DCs in an MSR-RITC-MSN scaffold over time. C57BL/6 mice are injected with the MSR-RITC-MSN scaffolds 1 day (MSRMSN-1d) and 7 days (MSR-MSN-7d) before recruited host immune cells are retrieved (n=4). A and B show the percentage of CD11c$^+$RITC$^+$ cells and representative flow cytometry dot plots, respectively. Data of A are expressed as the mean±SD, and analyzed by a two-tailed Student t-test. ***P<0.001.

Figure 11:
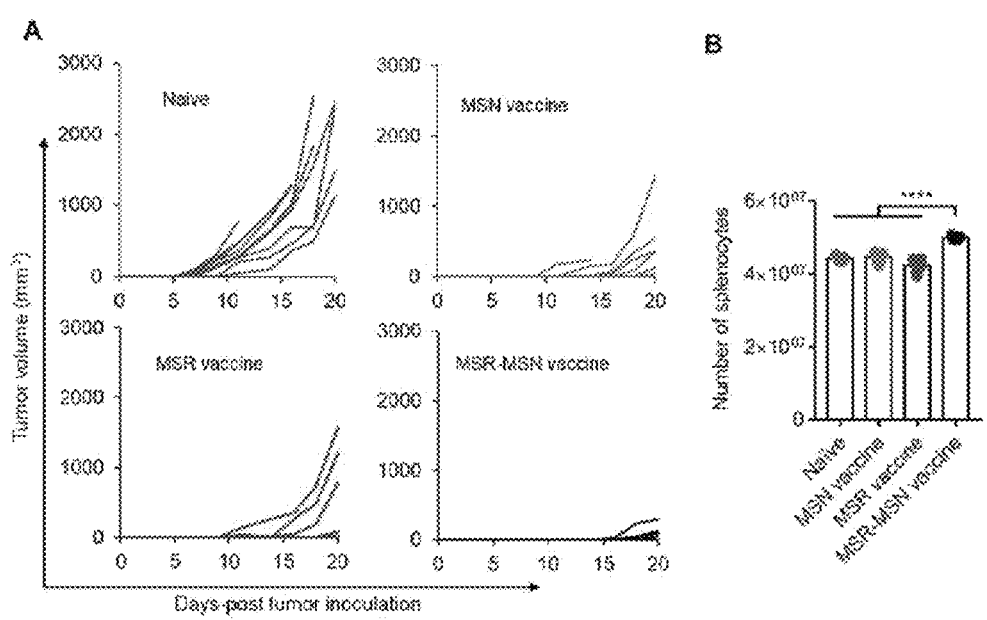

FIG. 11 shows that the MSR-MSN vaccine more effectively suppresses tumor growth than MSN and MSR vaccines. A shows tumor growth of animal subjects vaccinated with the MSN vaccine, the MSR vaccine, the MSR-MSN vaccine and no vaccine (naive) one week before tumor inoculation (n=10). B shows the number of splenocytes isolated from mice 7 days after vaccination with the MSN vaccine, the MSR vaccine, the MSR-MSN vaccine and no vaccine (naive) (n=5, mean±SD). Data of B are analyzed by one-way ANOVA. ****p<0.0001.

Figure 12:
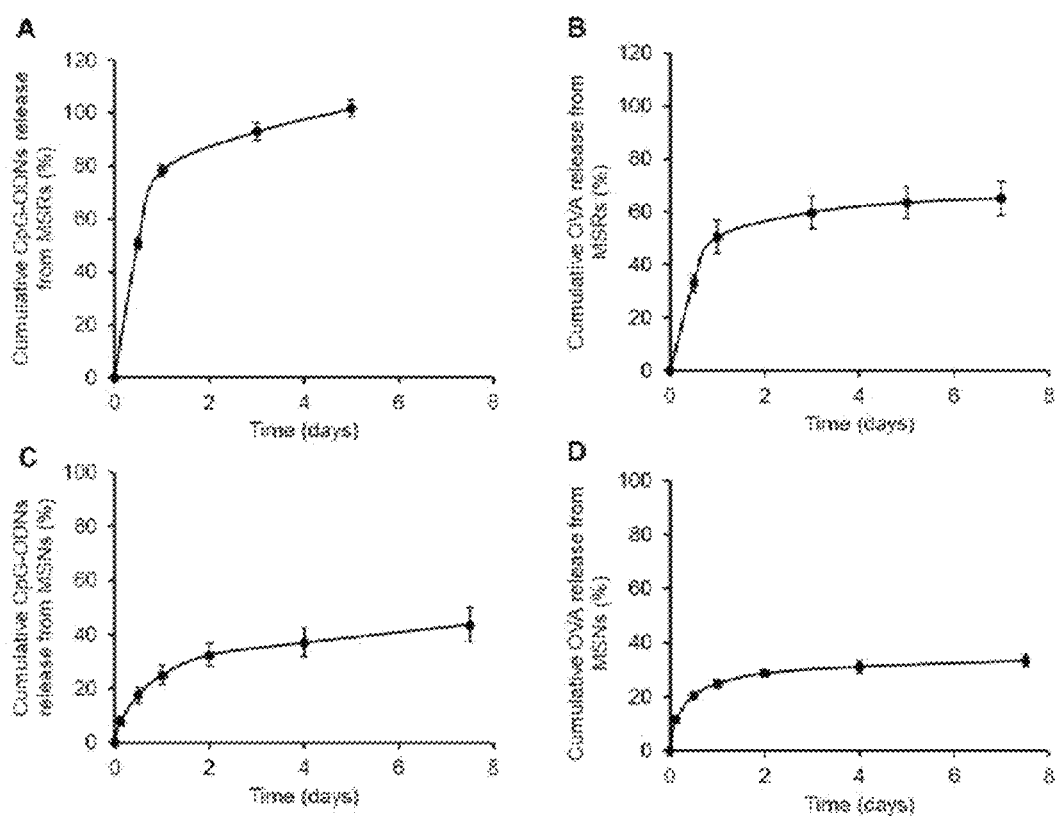

FIG. 12 shows a release profile. A and B show the cumulative release amounts of CpG-ODN and OVA released from MSR, respectively. C and D show the cumulative release amounts of CpG-ODN and OVA released from MSN, respectively. Data are expressed as the mean±SD.

MODES OF THE INVENTION

In one aspect of the present invention, the present invention provides a dual-scale porous silica particle-based pharmaceutical composition for preventing or treating cancer, which includes: (a) an antigen- and adjuvant-loaded porous silica nanoparticle; and (b) a porous silica microparticle carrying a chemoattractant attracting DCs.

In another aspect of the present invention, the present invention provides a dual-scale porous silica particle-based cancer vaccine pharmaceutical composition, which includes the (a) and (b).

In still another aspect of the present invention, the present invention provides a method of preventing or treating cancer, which includes administering the pharmaceutical composition to a subject in need thereof.

The term "prevention" used herein refers to all actions of inhibiting cancer or delaying the onset thereof by administration of the composition according to the present invention.

The term "treatment" used herein refers to all actions involved in alleviating or beneficially changing symptoms of cancer by administration of the composition according to the present invention.

The term "subject" used herein refers to a target in need of prevention or treatment of a disease. For example, the subject may be a mammal such as a human, a non-human primate, a mouse, a dog, a cat, a horse, sheep or a cow.

The term "dual-scale porous silica particle-based" used herein means that the composition of the present invention includes a porous silica nanoparticle and a porous silica microparticle, which have different scales (sizes), as active ingredients. For the purposes of the present invention, the scale of the porous silica nanoparticle is smaller than the porous silica microparticle.

Figure 1:
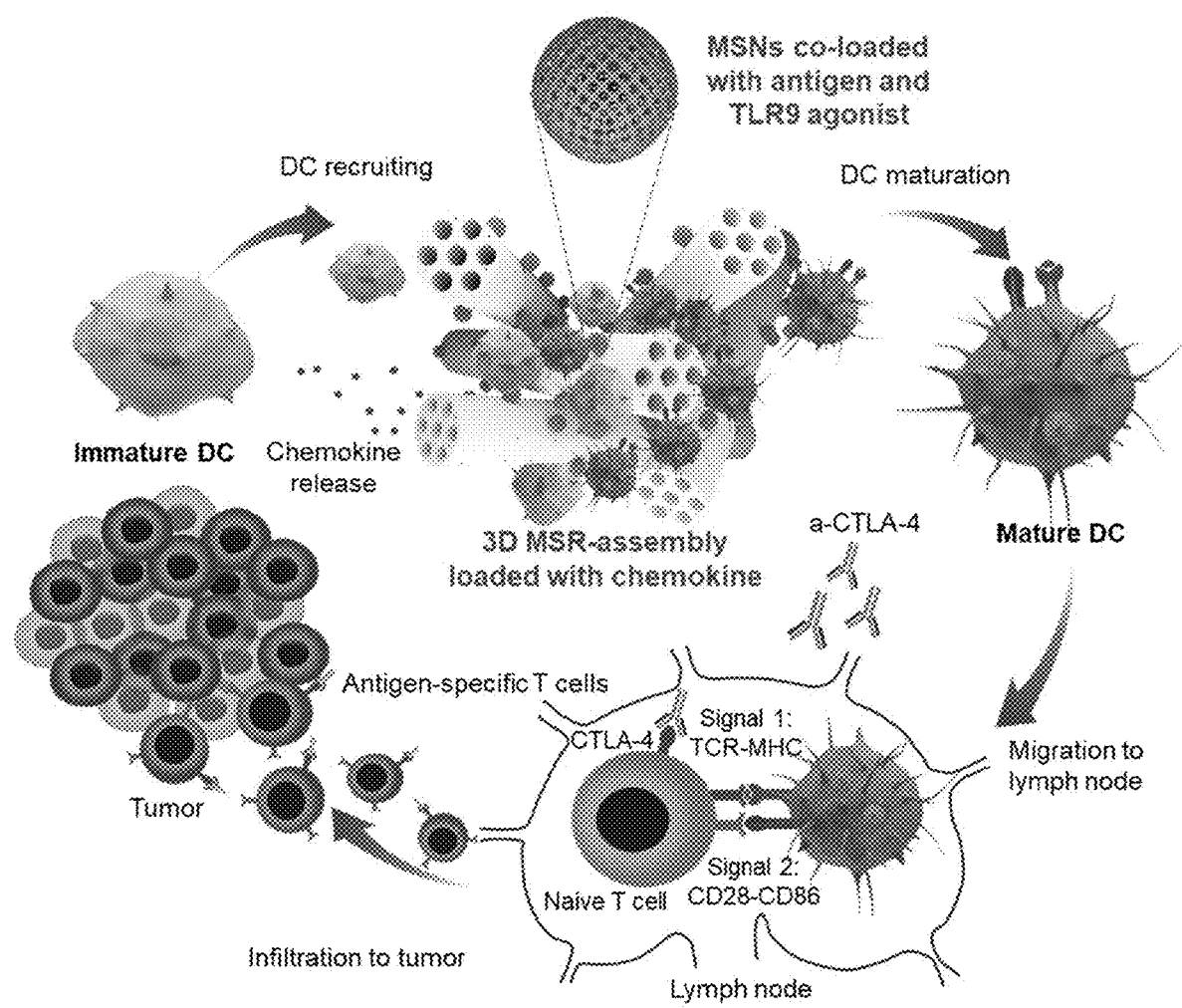
FIG. 1 is a schematic diagram illustrating the action mechanism of a dual-scale porous silica particle-based cancer vaccine according to one embodiment of the present invention.

Specifically, as shown in FIG. 1, the porous silica microparticle forms a 3D construct having a micro-sized space between the particles by self-assembly in the body, and a plurality of the porous silica nanoparticles are localized in the space of the 3D construct. Here, the porous silica nanoparticles may be localized in the space of the 3D construct while adsorbed onto the surface of the porous silica microparticle (see FIGS. 2A, A and B).

In the present invention, as a chemoattractant loaded in the porous silica microparticles forming the 3D construct is released, immature DCs may be recruited to the micro-scale space formed in the 3D construct. The recruited DCs enable the uptake of the porous silica nanoparticles carrying an antigen and an adjuvant, which have been located in the 3D construct. Afterward, the immature DCs which engulf the porous silica nanoparticles become mature, migrate to lymph nodes, and present the antigen to naive T cells to activate T cells, and therefore, activated antigen-specific cytotoxic T cells exhibit an anticancer action against cancer cells (see FIG. 1).

In the pharmaceutical composition of the present invention, the porous silica nanoparticles may carry an antigen and an adjuvant.

In the present invention, the antigen may be a cancer antigen (tumor antigen). The term "cancer antigen or tumor antigen" is an antigenic material generated in cancer cells, and a material causing an immune response in a host. For example, the cancer antigen may be a tumor cell lysate.

In the present invention, the antigen may include following materials:

MAGE-1, MART-1/MelanA, tyrosinase, a ganglioside, gp100, GD-2, O-acetylated GD-3, GM-2, Mucin 1, Sos1, a protein kinase C-binding protein, a reverse transcriptase protein, an AKAP protein, VRK1, KIAA1735, T7-1, T11-3, T11-9, *Homo sapiens* telomerase ferment (hTRP), cytokeratin-19 (CYFRA21-1), squamous cell carcinoma antigen 1 (SCCA-1), Protein T4-A, squamous cell carcinoma antigen 2 (SCCA-2), ovarian carcinoma antigen CA125 (1A1-3B) (KIAA0049), CTCL tumor antigen se1-1, CTCL tumor antigen se14-3, CTCL tumor antigen se20-4, CTCL tumor antigen se20-9, CTCL tumor antigen se33-1, CTCL tumor antigen se37-2, CTCL tumor antigen se57-1, CTCL tumor antigen se89-1, a prostate specific membrane antigen, a 5T4 oncofetal trophoblast glycoprotein, Orf73 Kaposi's sarcoma-associated herpesvirus, MAGE-C1 (cancer/testis antigen CT7), a MAGE-B1 antigen (MAGE-XP antigen), DAM10, a MAGE-B2 antigen (DAM6), a MAGE-2 antigen, a MAGE-4a antigen, a MAGE-4b antigen, colon cancer antigen NY-CO-45, lung cancer antigen NY-LU-12 variant A, a cancer-associated surface antigen, adenocarcinoma antigen ART1, a paraneoplastic associated brain-testis-cancer antigen, onconeural antigen MA2, a paraneoplastic neuronal antigen, neuro oncological ventral antigen 2 (NOVA2), hepatocellular carcinoma antigen gene 520, tumor-associated antigen CO-029, tumor-associated antigen MAGE-X2, colon cancer antigen 1, breast cancer antigen NY-BR-15, breast cancer antigen NY-BR-16, Chromogranin A, parathyroid secretory protein 1, DUPAN-2, CA 19-9, CA 72-4, CA 195 or a carcinoembryonic antigen (CEA).

In the present invention, the adjuvant may be selected from the group consisting of an activator (a toll-like receptor agonist or TLR agonist), an aluminum salt (aluminum hydroxide or aluminum phosphate), a saponin and a combination thereof. For example, the toll-like receptor activator may be a TLR1/2, TRL3, TRL4, TRL5, TRL7/8 or TRL9 activator, and the TLR1/2 activator includes triacylated lipoproteins (Pam3CSK4), the TLR3 activator includes dsRNA polyinosinic:polycytidylic acid (poly(I:C)), the TLR4 activator includes lipopolysaccharides (LPS), the TLR5 activator includes flagellin, the TLR7/8 activator includes imidazoquinolines (R848), the TLR2/6 activator includes diacylated lipoproteins (FSL-1), the TLR7 activator includes guanosine analogs (Loxoribine), the TLR9 activator includes a cytosine-guanosine oligonucleotide (CpG-ODN), and the TLR10 activator includes a profilin-like protein.

In the present invention, the antigen or adjuvant may be loaded in a manner selected from the group consisting of being loaded in pores of the porous silica nanoparticles, loaded by electrostatic attraction and a combination thereof.

In the present invention, the porous silica nanoparticles may be modified to have a positively or negatively charged surface. Due to the electrostatic attraction caused by the surface modification, a loading amount of the antigen and/or adjuvant may increase. In one exemplary embodiment, the porous silica nanoparticles may be modified to have a positively charged surface. For example, the porous silica nanoparticles may have a positively charged surface by amine modification or adsorption of a positively charged polymer such as polyethylenimine (PEI).

In the present invention, the porous silica nanoparticle may be a mesoporous silica nanoparticle (MSN).

In the present invention, the porous silica nanoparticle may be a 30 to 250-nm nanoparticle having a pore size of 3 to 30 nm.

In the pharmaceutical composition of the present invention, the porous silica microparticle may carry a chemoattractant to attract DCs.

The term "chemoattractant" used herein refers to a chemical material that is capable of attracting DCs to the 3D construct with a micro-scale space formed by the porous silica microparticles.

In the present invention, the chemoattractant may be selected from the group consisting of a granulocyte macrophage-colony stimulating factor (GM-CSF), chemokine (C-C motif) ligand 21 (CCL-21), chemokine (C-C motif) ligand 19 (CCL-19), FMS-like tyrosine kinase 3 (Flt-3) ligand and a combination thereof.

In the present invention, the porous silica microparticle may be rod-like, polygonal or spherical shaped.

In the present invention, the porous silica microparticle may be a mesoporous silica microrod (MSR).

In the present invention, the porous silica microparticle may have a length of 30 to 120 μm and a width of 5 to 30 μm.

In the present invention, the pharmaceutical composition of the present invention may have an increased anticancer effect according to an increase in content of porous silica nanoparticles or an adjuvant loaded in the porous silica nanoparticles (see Example 4). For example, the anticancer effect may be a cancer preventive effect.

In yet another aspect of the present invention, the present invention provides a pharmaceutical composition for cancer immunotherapy, which includes the pharmaceutical composition of the present invention and an immune checkpoint inhibitor.

The term "immune checkpoint inhibitor" used herein refers to a material that totally or partly suppresses, inhibits or controls one or more immune checkpoint proteins. The immune checkpoint proteins control the activation or function of T cells. Multiple immune checkpoint proteins, for example, PD-1, PD-L1 and CTLA-4, are known (Nature Reviews Cancer 12: 252-264, 2012). These proteins are involved in a co-stimulatory or suppressive interaction of T cell responses. The immune checkpoint inhibitor may include an antibody, and may be derived from an antibody.

In the present invention, the immune checkpoint inhibitor may be an antibody specifically binding to cytotoxic T-lymphocyte-associated protein 4 (CTLA-4), programmed cell death protein 1 (PD-1) or programmed death-ligand 1 (PD-L1). For example, the antibody specifically binding to CTLA-4 may be ipilimumab, the antibody specifically binding to PD-1 may be an antibody selected from the group consisting of pembrolizumab, nivolumab and cemiplimab, and the antibody specifically binding to PD-L1 may be an antibody selected from the group consisting of atezolizumab, avelumab and durvalumab.

Meanwhile, cancer that can be prevented or treated by the above-described pharmaceutical composition of the present invention includes blood cancer, colon cancer, brain cancer, glioma, stomach cancer, lung cancer, cervical cancer, colorectal cancer, rectal cancer, laryngopharyngeal cancer, lymphangiosarcoma, endometrial cancer, ovarian cancer, esophageal cancer, breast cancer, pancreatic cancer, prostate cancer, kidney cancer, liver cancer, Merkel cell carcinoma, bile duct cancer, chorionic carcinoma, testicular tumors, Wilm's tumor, Ewing's sarcoma, bladder cancer, hemangiosarcoma, papillary carcinoma, papillary adenosarcoma, bronchial cancer, melanoma, leiomyoma, urothelial carcinoma, head and neck cancer, rhabdomyoma, neuroblastoma, retinoblastoma, hemangioblastoma, bone cancer, fibrosarcoma, and leukemia.

In the present invention, the cancer may be selected from the group consisting of lung cancer, stomach cancer, glioma, liver cancer, melanoma, kidney cancer, urothelial carcinoma, head and neck cancer, Merkel cell carcinoma, prostate cancer, blood cancer, breast cancer, colon cancer, colorectal cancer, rectal cancer, pancreatic cancer, brain cancer, ovarian cancer, bladder cancer, bronchial cancer, skin cancer, cervical cancer, endometrial cancer, esophageal cancer, thyroid cancer, bone cancer and a combination thereof.

The above-described pharmaceutical composition of the present invention may further include a suitable carrier, excipient, and/or diluent that is/are conventionally used to prepare a pharmaceutical composition, in addition to the active ingredient. In addition, the pharmaceutical composition of the present invention may be formulated in the form of an oral form such as a powder, granule, capsule, suspension, emulsion, syrup or aerosol, a formulation for external use, a suppository or a sterile injectable solution according to a conventional method.

As a carrier, excipient and diluent capable of being included in the pharmaceutical composition, lactose, dextrose, sucrose, sorbitol, mannitol, xylitol, erythritol, maltitol, starch, acacia gum, alginate, gelatin, calcium phosphate, calcium silicate, cellulose, methyl cellulose, microcrystalline cellulose, polyvinyl pyrrolidone, water, methylhydroxy benzoate, propylhydroxy benzoate, talc, magnesium stearate, and mineral oil are used. When the composition is formulated, a common diluent or excipient such as a filler, a thickening agent, a binder, a wetting agent, a disintegrating agent or a surfactant may be used for formulation.

The pharmaceutical composition according to the present invention is administered at a pharmaceutically effective amount. In the present invention, the "pharmaceutically effective amount" used herein refers to an amount sufficient for treating a disease at a reasonable benefit/risk ratio applicable for medical treatment, and an effective dosage may be determined by parameters including a type of a patient's disease, severity, drug activity, sensitivity to a drug, administration time, an administration route and an excretion rate, the duration of treatment and drugs simultaneously used, and other parameters well known in the medical field.

As a specific example, the pharmaceutical composition may be administered once or several times at a daily dose of 0.001 to 1000 mg/kg, 0.05 to 200 mg/kg or 0.1 to 100 mg/kg, and may be administered at a weight-based dose as well as a flat-dose once when needed. A preferable dose may be selected according to the condition and body weight of a subject, the severity of a disease, a dosage form, an administration route and duration.

In consideration of all the above-mentioned parameters, it is important to achieve the maximum effect with the minimum dose without a side effect, and such a dose may be easily determined by one of ordinary skill in the art. Specifically, the effective amount of the pharmaceutical composition according to the present invention may vary according to the age, sex, condition and body weight of a patient, the uptake of an active ingredient in the body, an inactivation rate, an excretion rate, the type of disease, and a drug used in combination.

The pharmaceutical composition of the present invention may be administered to a subject via various routes. All administration modes may be expected, and the pharmaceutical composition of the present invention may be administered by intraarterial injection, intravenous injection, subcutaneous injection, oral administration, intranasal administration, transbronchial administration, intramuscular injection or intraperitoneal injection. The daily dose may be administered once to several times a day.

Hereinafter, to help in understanding the present invention, exemplary examples will be suggested. However, the following examples are merely provided to more easily understand the present invention, and not to limit the present invention.

EXAMPLES

Experimental Materials and Methods

1. Experimental Materials

Tetraethyl orthosilicate (TEOS), Pluronic P123 (average Mn=5800), ammonium fluoride (NH$_4$F), hexadecyltrimethylammonium bromide (CTAB), an ammonium hydroxide solution, (3-aminopropyl)triethoxysilane (APTMS), OVA, rhodamine B isothiocyanate (RITC), phorbol 12-myristate 13-acetate (PMA), ionomycin and RPMI-1640 were purchased from Sigma-Aldrich.

A murine granulocyte-macrophage colony-stimulating factor (GM-CSF) was purchased from PeproTech (315-03). Ethanol, methanol, hydrochloric acid and ethyl acetate were purchased from Samchun (Seoul, Korea). CpG-ODN was purchased from Genotech (Daejeon, Korea).

2. Antibodies

An FcR blocking reagent, CD11b-PE-Vio770, MHC class II-FITC, CD4-PE-Vio770, CD8-APC, IFN-γ-FITC. H-2Kb monoclonal antibodies and their isotypes were purchased from Miltenyi Biotec (Germany). CD11c-APC, CD86-eFluor450 monoclonal antibodies and their isotypes were purchased from eBioscience. Tetramer-SIINFEKL-PE was purchased from MBL (Japan). All flow cytometric analyses were performed using MACSQuant VYB (Miltenyi Biotec).

3. Preparation and Characterization of Mesoporous Silica Microrods (MSRs)

4 g of block copolymer Pluronic P123 was dissolved in 130 mL of deionized (DI) water containing 46 mg of ammonium fluoride and 20 mL of hydrochloric acid. The prepared solution was stirred with 8.6 g of a silica precursor (TEOS, 98%) at 40° C. for 20 hours, followed by aging at 100° C. for 24 hours. The resulting solution was then filtered, washed with ethanol and dried to obtain MSR powder. Finally, the Pluronic P123 was removed by heating the powder at 550° C. for 5 hours. Particle morphology was examined through TEM and SEM. The pore size, pore volume and surface area were measured by a Brunauer-Emmett-Teller (BET) method.

4. Synthesis and Characterization of Mesoporous Silica Nanoparticles (MSNs)

500 μL of Fe$_3$O$_4$ (6 mg/mL) nanocrystals (diameter: 6 nm), which were synthesized by a heat-up method from an iron-oleate complex, was poured into 10 mL of a 0.055 M CTAB aqueous solution with vigorous stirring for 30 minutes. The obtained solution was heated at 60° C. for 15 minutes, and added to a solution containing 95 mL of DI water, 5 mL of methanol, 3 mL of an ammonium hydroxide solution and 20 mL of ethyl acetate. Subsequently, 500 μL of TEOS was added to the mixed solution, and stirred overnight. The resulting MSNs were washed with ethanol three times before storage in 40 mL of ethanol. The MSNs were stirred in acidic ethanol containing HCl at 60° C. for 3 hours to extract CTAB, and remove a Fe$_3$O$_4$ nanocrystal core. Finally, the obtained MSNs were washed with ethanol three times, and stored in 30 mL of ethanol for further experiments. The pore size and volume of MSN were analyzed using a BET method.

5. Amine Modification and RITC Conjugation of MSNs

APTMS was added to an MSN solution (the molar ratio of TEOS:APTMS=10:1) and allowed to react overnight. Afterward, the particles were washed with ethanol three times. To track MSNs in vivo, RITC (a molar ratio of 1:10) was added with APTMS to 750 μL of ethanol (anhydrous, 99.9%) under a dark condition for 24 hours in order to form RITC-APTMS, and RITC-labeled MSNs were prepared. The RITC-APTMS was added with TEOS, thereby obtaining an RITC-labeled MSN (RITC-MSN).

6. Vaccine Preparation

To prepare an MSN vaccine, first, 1 mg of amine-modified MSNs were mixed with an OVA solution dissolved in PBS to prepare a final concentration of 5 mg OVA/mL. The mixture was rotated for 2 hours before being washed with PBS three times. An MSN-free PBS supernatant was obtained during washing to confirm an OVA loaded amount through ultraviolet-visible (UV-vis) absorbance at 280 nm. Subsequently, the OVA-loaded MSNs were mixed with a CpG-ODN solution in 500 μL of PBS for 30 minutes, and then washed three times. During washing, the CpG-ODN supernatant was obtained to calculate a loaded amount of CpG-ODN, and the UV-Vis absorbance was measured at 263 nm.

To prepare an MSR-MSN vaccine, 5 mg of MSRs were mixed with 1 μg of GM-CSF (1 mg/mL) for 4 hours and lyophilized, and then stored at −20° C. until injection. Right before the vaccination, 200 μL of the MSN vaccine was well mixed with GM-CSF-loaded MSRs to prepare the MSR-MSN vaccine. The vaccine was subcutaneously injected into the mouse flank using a standard 17G needle.

7. In Vitro GM-CSF Release Test 5 mg of MSRs were mixed with 1 μg of GM-CSF (1 mg/mL) for 4 hours, followed by lyophilization. Subsequently, the GM-CSF-loaded MSRs were resuspended, and gently shaken in a 1 mL release medium consisting of RPMI (Sigma-Aldrich) supplemented with 1% penicillin-streptomycin and 10% heat-inactivated FBS (Merck Millipore) at 37° C. The supernatant containing GM-CSF was periodically collected, and then replaced with fresh RPMI. The released GM-CSF was measured by ELISA (R&D).

8. In Vitro CpG-ODN Release from MSRs and MSNs 5 mg of MSRs were mixed with 50 μg of CpG-ODN for 4 hours, followed by lyophilization. Subsequently, the CpG-ODN-loaded MSRs were resuspended in PBS under a gentle shaking condition at 37° C. A supernatant containing the released CpG-ODNs was collected, and then periodically replaced with a fresh medium. The concentration of the released CpG-ODNs was measured by UV-Vis absorbance at 263 nm.

The MSN vaccine containing cyanine 5-conjugated CpG-ODNs was gently shaken at 37° C. to release CpG-ODNs in PBS. The supernatant was collected, and replaced with a fresh medium over time. The released CpG-ODNs were measured by monitoring fluorescence excitation and emission at 650 nm and 669 nm, respectively.

9. In Vitro OVA Release from MSRs and MSNs 5 mg of MSRs were used for OVA adsorption (200 μg) for 4 hours, followed by lyophilization. Subsequently, the OVA-loaded MSRs were resuspended in PBS under a gentle shaking condition at 37° C. The released OVA was collected, and then the medium was periodically replaced with a fresh medium. The OVA concentration was measured using a Pierce BCA Protein Assay kit (Thermo Fisher).

OVA loaded in amine-functionalized MSNs was gently shaken at 37° C. to release it in PBS. The supernatant was collected, and the medium was replaced with a fresh medium overnight. The released OVA was detected using a Pierce BCA Protein Assay kit.

10. Analysis of Recruited Cells from Scaffold

The nodules generated at vaccinated sites were removed from the body on day 1 and day 7 after injection, and the cells recruited in the nodules were isolated under a collagenase type IV (1 mg/mL, Gibco) condition in RPMI at 37° C. for 15 minutes. The cell suspension mixed with MSRs was filtered using a 40-μm cell strainer to remove the MSRs. Subsequently, the cells were washed and counted in cold PBS, followed by staining with a FcR blocking reagent and then antibodies against CD11c, CD11b, CD86 and MHC-II at 4° C. for 15 minutes. Finally, the cells were washed, and then analyzed using a flow cytometer.

11. Analysis of Lymph Node Cells

Inguinal lymph nodes near an injection site were removed, and then cells in the lymph nodes were isolated by mechanical disruption and filtered using a 40-μm cell strainer in cold PBS. Subsequently, the cells were counted, and $10^6$ cells from each sample were first stained with an FcR blocking reagent, followed by staining with antibodies against CD11c, CD86 and MHC-II in a dark place at 4° C. for 15 minutes. Finally, LN cells were washed, and subjected to flow cytometry.

12. Tumor Experiment 6-8-week-old C57BL/6 mice were purchased from OrientBio (Korea). For a prophylactic experiment, different vaccine formulations were subcutaneously injected into the mice 1 week before tumor inoculation ($5 \times 10^5$ mycoplasma-free B16-OVA (ATCC) cells per mouse). For the prophylactic experiment, $5 \times 10^5$ B16-OVA cells were subcutaneously injected into each mouse before vaccination. CTLA4 antibodies were intraperitoneally injected at a dose of 100 μg per mouse. A tumor volume (V) was calculated using the following formula: V (mm$^3$)=(Length×Width$^2$)/2 using a caliper. The mice were euthanized via $CO_2$ asphyxiation. All animal experiments were performed according to the protocol of Sungkyunkwan University Institutional Animal Care and Use Committee (SKKUIACUC).

13. Cellular Immune Response in Spleen

Seven days after immunization, the spleen was excised and processed to prepare a cell suspension in cold PBS. Subsequently, red blood cells were lysed using an ACK lysing buffer (Lonza) and washed with cold PBS. A small amount of the cell suspension was used to calculate the total cell number. For flow cytometry, $10^6$ cells from each sample were first stained with an FcR blocking reagent, and stained with antibodies against CD4 and CD8 for 15 minutes and then H-2K$^b$ tetramer-SIINFEKL for 30 minutes in a dark place at 4° C. Finally, the cells were washed with FACS buffer containing 0.5% BSA, followed by flow cytometry analysis. For intracellular staining, $10^6$ splenocytes were stimulated with complete RPMI-1640 containing 100 ng/mL of PMA and 1 μg/mL of ionomycin for 6 hours, and for the last four hours, stimulated in the presence of BD GolgiStop. Subsequently, the splenocytes were washed, and stained with a surface marker. The cells were fixed, permeabilized and then stained intracellularly with antibodies against IFN-γ, before flow cytometry analysis.

14. Flow Cytometry

Flow cytometry data was analyzed by FlowJo X 10.0. In all cases, cells were first gated on FSC-A/SSC-A. Subsequently, single cells were gated using FSC-H/FSC-H. Then, surface and intracellular antigen gating was performed.

15. Statistical Analysis

All values in this study were expressed as the mean±SD. For statistical analysis, Graphpad Prism 7.00 was used. The significance between two groups was analyzed using a Student t-test. For multiple comparison, one-way ANOVA was used. In all cases, statistical differences were considered significant at P<0.05, and represented as *P<0.05, P<0.01, *P<0.001 and ****P<0.0001.

Experimental Results

Example 1. MSR-MSN Vaccine Enhanced DC Uptake and Migration of MSNs to dLN Over Time A dual-scale mesoporous silica vaccine was prepared by combining MSNs loaded with OVA and CpG-ODN and MSRs loaded with GM-CSF. An MSN vaccine carrying OVA and CpG-ODN was prepared using large-pore MSNs of approximately 150 nm in diameter with a mesopore size of 20-30 nm. To increase a loaded amount of CpG-ODNs, which are negatively-charged single-stranded DNA molecules, the MSNs were modified by a silane coupling chemical reaction using (3-aminopropyl)trimethoxysilane to provide an amine terminus on the MSN surface.

Figure 2A:
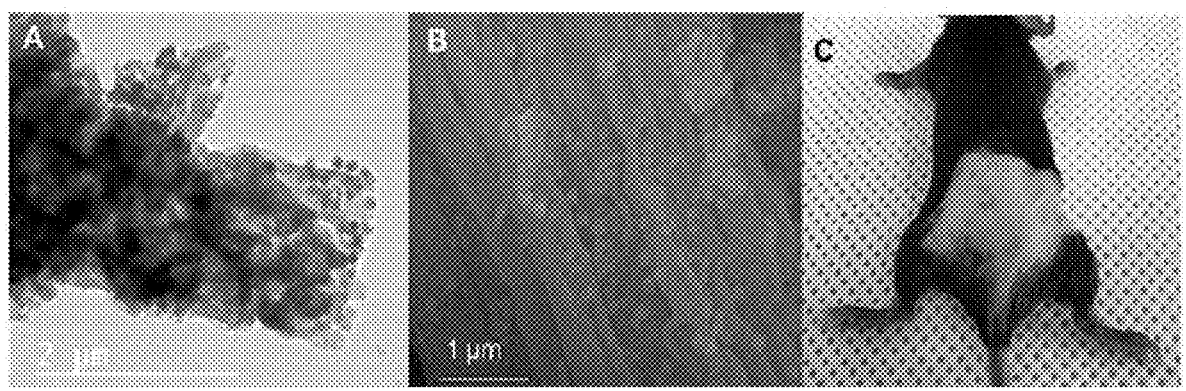
FIG. 2A shows TEM (A) and SEM images (B) of an MSR-MSN dual particle platform, and an image (C) of a mouse into which GM-CSF-loaded MSR-MSN is subcutaneously injected on day 7. C57BL/6 mice have been injected with MSR-RITC-MSN vaccines one day (MSR-MSN-1d) and 7 days (MSR-MSN-7d) before recruited immune cells are retrieved (n=4)

High-aspect-ratio MSRs (average length: 86 μm, width: 14.5 μm) having distinct mesoporous characteristics were prepared. GM-CSF-loaded MSRs were prepared by inducing physical adsorption of GM-CSF onto MSR. As observed by transmission electron microscopy (TEM) and scanning electron microscopy (SEM), MSNs were distributed on the surface of MSRs by the combination of the GM-CSF-loaded MSRs and MSN vaccine (loaded with OVA and CpG-ODNs) (FIGS. 2A, A and B). The zeta potentials of MSRs and GM-CSF-loaded MSRs were slightly negative and neutral, respectively, and the zeta potentials of the MSN vaccine was negative (FIG. 7). Therefore, there was no significant electrostatic interaction between MSRs and the MSN vaccine. Small MSNs can be physically adsorbed onto the surface of large MSRs through van der Waals interactions and hydrogen bonds, so that the combined nanovaccine is a mixture rather than a composite. Therefore, the recruited DCs can absorb small MSNs in a 3D scaffold constructed by randomly-assembled MSRs.

Figure 2B:
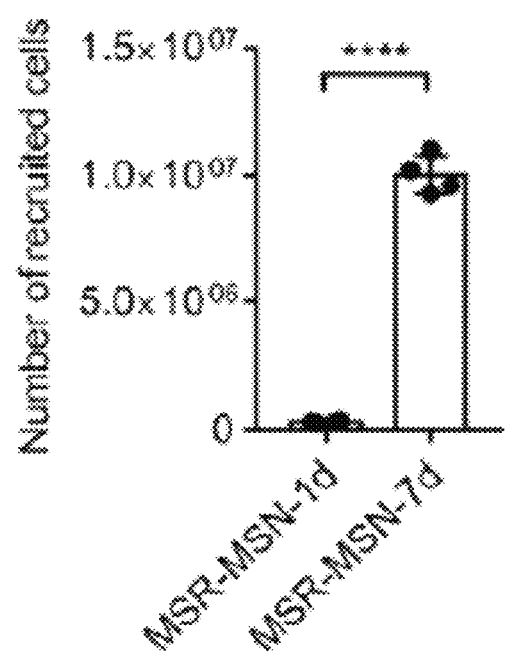
FIGS. 2B and 2C show the numbers of recruited immune cells and CD11c$^+$CD11b$^+$ dendritic cells, which are attracted by an MSR-MSN scaffold on day 1 and day 7, respectively.
Figure 2C:
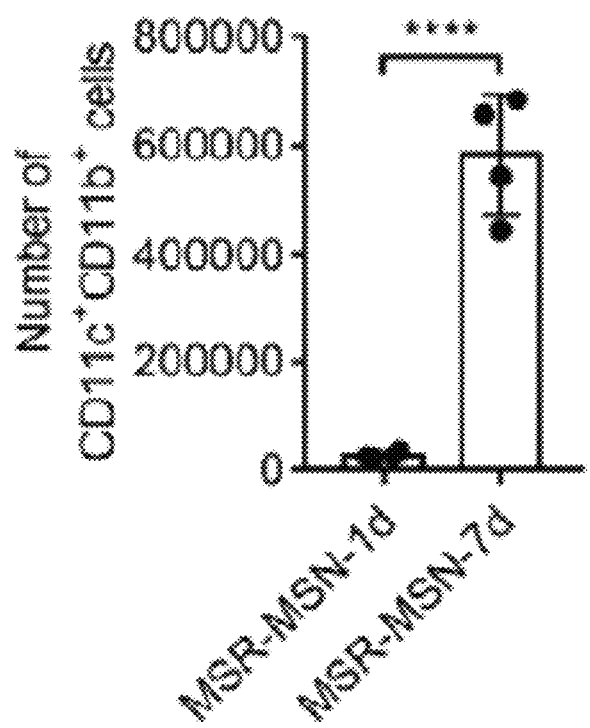

The inventors investigated whether the DC-recruiting scaffold enhanced MSN delivery into the peripheral DCs recruited to the injection site. The subcutaneous injection of GM-CSF-loaded MSRs combined with the MSN vaccine into C57BL/6 mice resulted in the formation of a subcutaneous nodule at the mouse flank after 7 days (FIG. 2A, C). According to observation during the experimental period, the injection of an MSR-MSN platform did not cause discomfort and severe inflammation in the animals. The nodule was completely deteriorated after a month due to the degradation of MSRs under in vivo physiological conditions [Y. Choi et al., Langmuir. 31 (2015) 6457-6462]. The recruitment of a large number of host immune cells was observed in the retrieved nodule (FIG. 2B) due to the sustained release of GM-CSF from the MSR scaffold (FIG. 8A). The analysis of the retrieved cells from the nodule revealed that approximately $2.5 \times 10^4$ and $5.8 \times 10^5$ conventional $CD11c^+CD11b^+$ DCs had infiltrated into interparticle macropores of the MSR scaffold on day 1 and day 7 after injection (FIG. 2C), corresponding to 9% and 5.82% of the total recruited cells, respectively (FIGS. 8B and 8C).

Figure 2D:
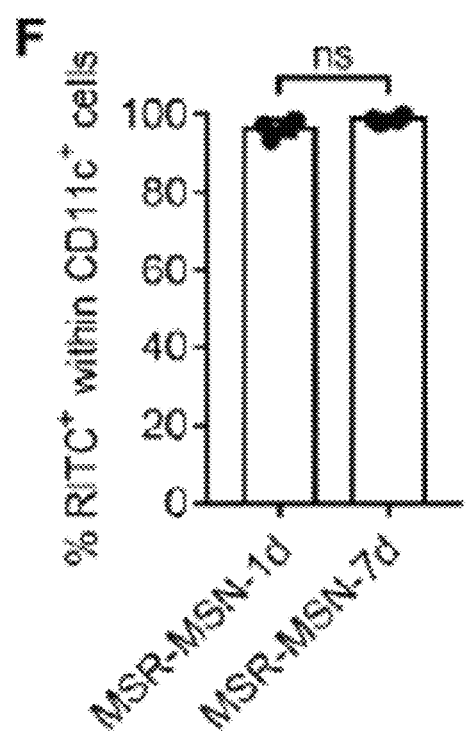
FIG. 2D shows the percentage of RITC within a CD11c$^+$ cell population.
Figure 2E:
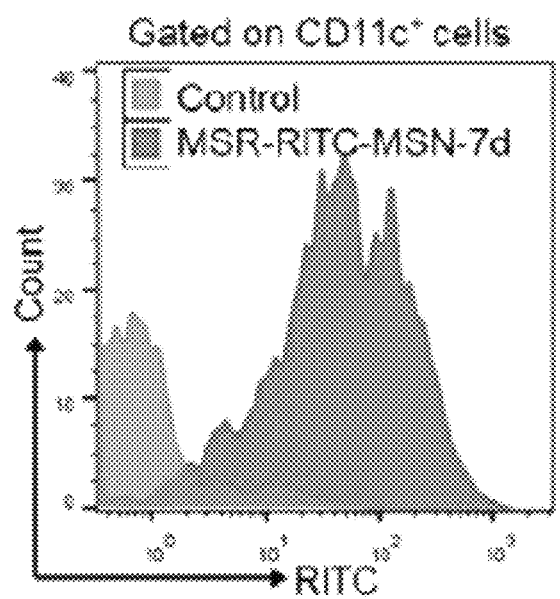
FIG. 2E shows a representative histogram of RITC signals for CD11c$^+$ cells retrieved from an MSR scaffold (control) and an MSR-MSN (RITC) scaffold on day 7.
Figure 2F:
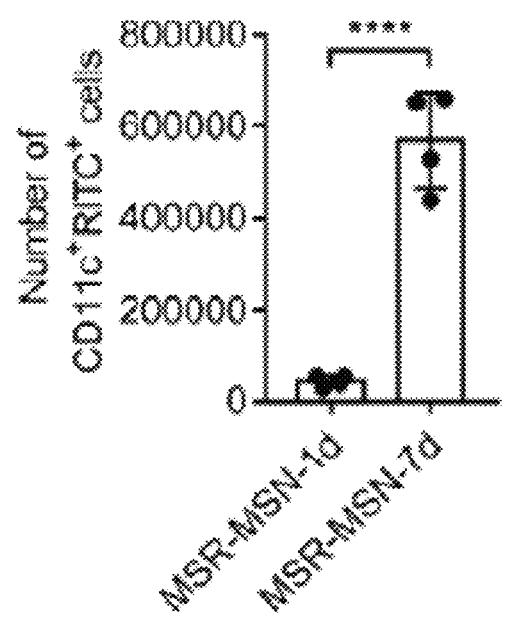
FIG. 2F shows the number of CD11c$^+$RITC$^+$ cells retrieved from an MSR-MSN vaccine on day 1 and day 7.
Figure 2G:
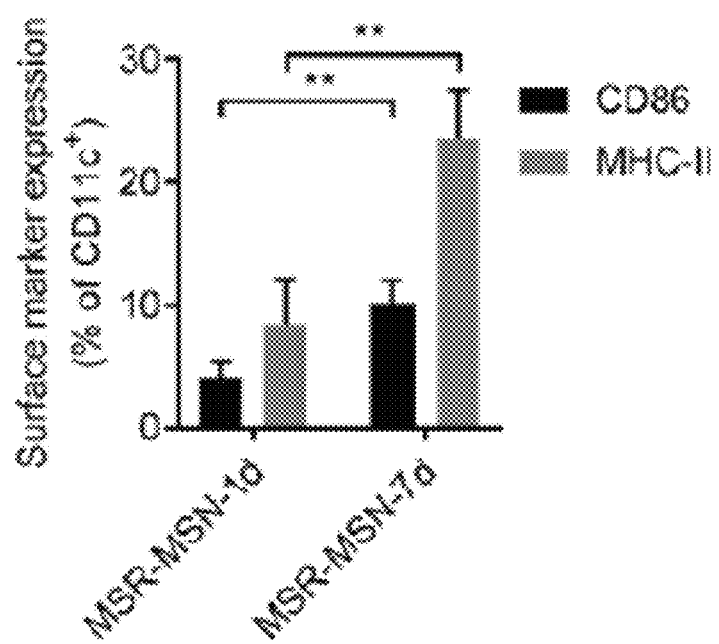
FIG. 2G shows the expression of CD86 and MHC-II in the recruited CD11c$^+$ cells of the MSR-MSN scaffold on day 1 and day 7. Cells are isolated from inguinal LNs of animals vaccinated with an RITC-MSN vaccine or MSR-RITC-MSN vaccine or not vaccinated on day 1 and day 7 after injection (n=4)

To investigate the recruited DC engulfment of MSNs, an MSR-MSN dual-scale system prepared using RITC-labeled MSNs (FIG. 9) and RITC-labeled MSNs (RITC-MSN) alone were injected into the animals. After collecting the nodules and isolating the recruited cells on day 1 and day 7 after injection, RITC DCs among the cells retrieved from the nodule were analyzed by a flow cytometer. Interestingly, most of the recruited $CD11c^+$ DCs had engulfed RITC-MSN (FIGS. 2D and 2E), and a considerable amount of RITC DCs were found on day 7 (FIG. 2F), indicating that MSNs released from the surface of MSRs were internalized by the recruited, phagocytic, immature DCs. The continuous release of GM-CSF over time probably reduced the zeta potential of an MSR, which may induce the gradual separation of the negatively-charged MSN vaccine from an MSR surface may occur. As a result, the cellular uptake of MSNs improved the expression of CD86 and MHC-II in the recruited DCs over time (FIG. 2G), which is necessary for subsequent T cell activation in dLNs. The percentage of $CD11c^+RITC^+$ cells in the MSR-MSN scaffold was decreased over time (FIGS. 10A and 10B), probably indicating that the RITC DCs moved from the vaccination site to dLNs. As a large amount of DCs were recruited to the MSR scaffold due to a released chemoattractant, the MSNs present in the same place had a higher probability of encountering immature DCs.

Figure 2H:
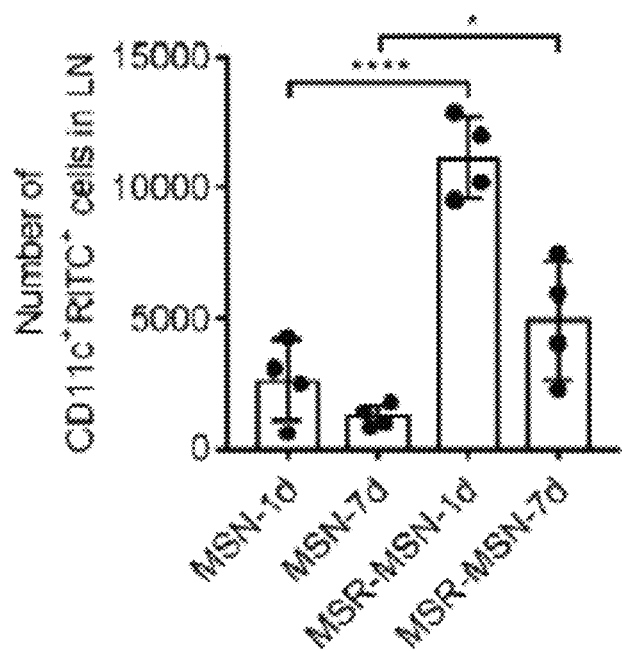
FIGS. 2H, 2I and 2J show CD11c$^+$RITC$^+$ cells, CD11c$^+$CD86$^+$ cells and CD11c$^+$MHC-II$^+$ cells in inguinal LNs, respectively, wherein the data in FIGS. 2B, 2C and 2F to 2J is expressed as mean±standard deviation (SD). The data in FIGS. 2B, 2C, 2D, 2F and 2G is analyzed by a two-tailed Student t-test. One-way ANOVA is applied to the data in FIGS. 2H, 2I and 2J.
Figure 2I:
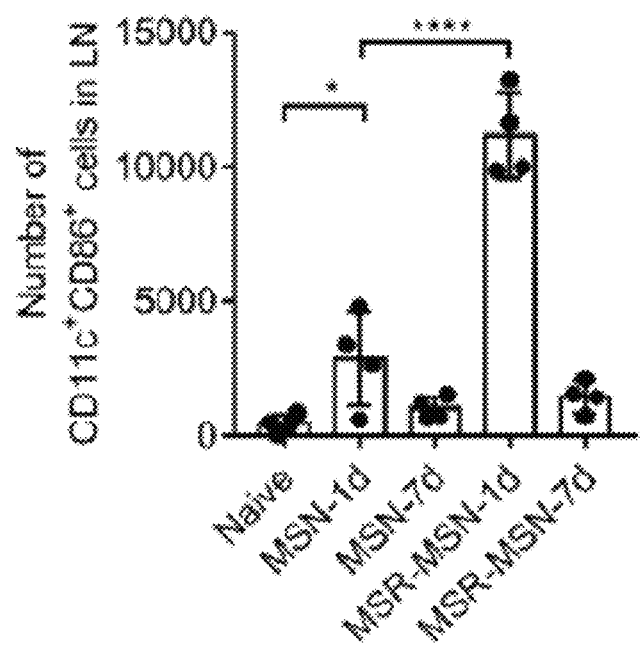
Figure 2J:
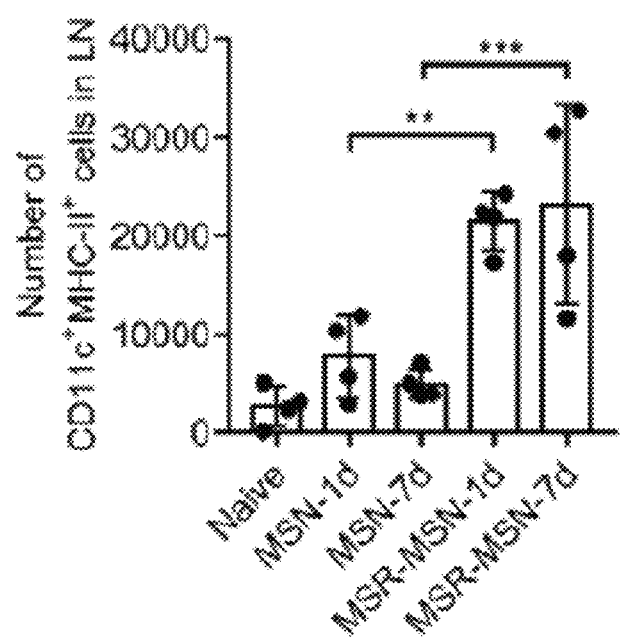

When MSNs were subcutaneously injected, most particles were spread around the injection site, and some of them were observed in the inguinal lymph node within 24 hours after injection, which is typical for nanoparticle vaccines [B. G. Cha et al, ACS Cent. Sci. 4 (2018) 484-492]. On the other hand, the inventors hypothesized that some MSNs of the MSR-MSN vaccine may not only passively migrate to dLNs through an afferent lymphatic vessel, but some MSNs may also be maintained in the interparticle space of the 3D scaffold, and enter dLNs by the uptake of a considerable amount of recruited DCs. To prove this, on day 1 and day 7 after subcutaneous injection of the MSR-MSN (RITC) vaccine and the MSN (RITC) vaccine, the accumulation of RITC-MSNs in the inguinal LN near the injection site was analyzed. The number of $CD11c^+RITC^+$ cells from the LN of MSR-MSN vaccinated mice was 4-fold higher than that of MSN vaccinated mice both on day 1 and day 7 after injection, indicating that the MSR-MSN vaccine helped the migration of nanovaccines to dLNs over time (FIG. 2H). The high local concentration of the MSN vaccine in a macroporous scaffold where DCs are continuously recruited through the continuous release of GM-CSF is advantageous for long-term activation and antigen presentation of peripheral DCs. Consistent with DC activation in nodules (FIG. 2G), DCs in the inguinal LN of MSR-MSN vaccinated mice showed higher expression of CD86 (FIG. 2I) and MHC-II (FIG. 2J) compared to MSN vaccinated mice.

Taken together, these results indicate that the enhanced phagocytosis of DCs for MSNs in the DC-recruited MSR scaffold and subsequent gradual homing of MSN-internalized DCs to dLNs considerably increased the number of activated DCs in the LN, and are caused by an MSR-MSN dual-scale vaccine. Moreover, the long-term maintenance of the MSN vaccine serving as antigen and adjuvant reservoirs in dLNs imitates prime-boost immunization after single administration [M. S. Goldberg et al., Cell. 161 (2015) 201-204].

Example 2. In Vivo Induction of Antigen-Specific T Cell Response Against Melanoma Next, it was investigated whether a dual-scale vaccine can enhance an antigen-specific antitumor immune response in a mouse tumor model. C57BL/6 mice were vaccinated with the MSN vaccine (OVA and CpG-ODN-loaded MSNs) or MSR-MSN vaccine (consisting of GM-CSF-loaded MSRs, and OVA and CpG-ODN-loaded MSNs), and inoculated with B16-OVA melanoma cells 7 days after vaccination, and then a tumor volume was measured over time (FIG. 3A). The amounts of the antigen (OVA) and adjuvant (CpG-ODN) loaded in each vaccine were the same. The MSN-vaccinated mice exhibited a considerable tumor suppressive effect compared to non-vaccinated control mice. Surprisingly, even more significant tumor suppression was observed for the mice vaccinated with the MSR-MSN vaccine (FIGS. 3B and 3C). On day 20, all mice were sacrificed, and the splenocytes were collected and analyzed to detect antigen-specific $CD8^+$ T cells. The percentage of $H-2K^b$ OVA (SIINFEKL) tetramer$^+$ among the $CD8^+$ T cells in the spleens of the animals vaccinated with the MSR-MSN vaccine was 2-fold higher than the mice vaccinated with the MSN vaccine (FIGS. 3D and 3F). Similarly, the percentages of IFN-$\gamma^+$ among $CD8^+$ T cells in the animals vaccinated with the MSR-MSN vaccine were 3.2- and 2-fold higher than the control mice and the mice vaccinated with MSN vaccine, respectively (FIGS. 3E and 3F).

These results indicate that the MSR-MSN vaccine is more powerful than the MSN vaccine for inducing a systemic antigen-specific cellular immune response against cancer. The improved efficacy of the nanovaccine caused by the DC-attracting macroporous scaffold shows the critical role in adaptive immunity induction of the prolonged recruitment of DCs to a local site where the nanovaccine is located.

Example 3. MSR-MSN Dual-Scale Vaccine Suppressed Tumor Growth More Effectively than MSN or MSR Vaccine In addition, it was investigated whether the dual-scale vaccine has a better effect than the MSR vaccine emerging as an effective injectable cancer vaccine platform. In the MSR vaccine, GM-CSF, OVA and CpG-ODN were simultaneously loaded in 9.74-nm mesopores of MSRs with a negatively-charged hydroxyl surface. Therefore, due to a difference in electrostatic interactions with OVA (slightly negative charge) and CpG-ODN (highly negative charge), separate releases of the antigen and adjuvant occurred.

However, to effectively activate DCs, both the antigen and adjuvant have to be delivered simultaneously to immature DCs. The inventors considered that positively-charged amine-modified MSNs can strongly hold both OVA and CpG-ODN through electrostatic interactions, which may be advantageous for the activation of recruited DCs compared to the separate releases of soluble OVA and CpG-ODN from the MSR vaccine. Accordingly, the inventors compared efficiency of the MSR-MSN, MSR and MSN vaccines (FIG. 4A). For accurate comparison, the same doses of GM-CSF, CpG-ODN and OVA were loaded in the same amounts of MSRs and/or MSNs according to a vaccine type. Specifically, an MSN (111 μg) vaccine was prepared by loading OVA (100 μg) and CpG-ODN (10 μg); and an MSR (5 mg) vaccine was prepared by loading GM-CSF (1 μg), OVA (100 μg) and CpG-ODN (10 μg); and an MSR-MSN vaccine was prepared by mixing GM-CSF (1 μg)-loaded MSR (5 mg), and OVA (100 μg) and CpG-ODN (10 μg)-loaded MSNs (111 μg) (FIG. 4B). Subsequently, 7 days before tumor inoculation, C57BL/6 mice were immunized with the MSN, MSR and MSR-MSN vaccines, and the tumor size was measured over time (FIG. 4C).

The MSR-MSN vaccine exhibited a much higher tumor suppression effect than the MSN and MSR vaccines (FIG. 4D and FIG. 11A). In addition, the MSR-MSN vaccine completely protected the animals from tumors for 15 days after tumor inoculation (FIG. 4E), and the survival rate of the animals was much higher than the other groups (90% survival rate 26 days after tumor inoculation, FIG. 4F).

Subsequently, the level of a cell-mediated immune response after immunization of the vaccine groups was investigated. Interestingly, the mice vaccinated with the MSR-MSN vaccine exhibited more splenocytes than the other groups (FIG. 11B). The MSR and MSR-MSN vaccines induced a larger number of OVA (SIINFEKL)-specific $CD8^+$ T cells than the MSN vaccine in the mouse spleen (FIG. 4G). However, compared with the MSN vaccine, the percentage of OVA (SIINFEKL)-specific $CD8^+$ T cells was increased to a further higher level by the MSR-MSN vaccine than the MSR vaccine (FIGS. 4H and 4I). The burst release of CpG-ODN (80%) and OVA (50%) from MSRs was observed after one day (FIGS. 12A and 12B), and the number of recruited DCs on one day 1 after injection was limited, which shows that CpG-ODN and OVA cannot be well controlled for optimal DC uptake over time when loaded in MSRs. On the other hand, when an antigen and an adjuvant are loaded in amine-modified large-pore mesoporous silica nanoparticles (MSNs), the antigen and the adjuvant may be simultaneously delivered to the recruited DCs when the DCs engulf the MSNs. In addition, the release rates of negatively-charged CpG-ODNs and slightly negatively-charged OVA from the positively-charged, amine-modified large-pore MSNs were relatively similar due to electrostatic interactions, and the release continued over a long period of time (FIGS. 12C and 12D). These results show that the simultaneous delivery of the antigen and adjuvant loaded in nanoparticles to the DCs recruited in the scaffold is advantageous for initiating DC activation and antigen cross-presentation compared with the separate release from the macroporous scaffold. Therefore, the incorporation of the MSN vaccine into MSRs may surpass the efficacy of the current nanoparticle- or microporous scaffold-based vaccine system.

Example 4. Optimized Vaccine Formulation with Highest Efficacy

Next, it was investigated whether the efficacy of the MSR-MSN vaccine can be improved by optimizing doses of MSN, an adjuvant and an antigen. As a consistent DC-recruiting microporous scaffold platform under all conditions, 5 mg of MSRs loading 1 μg of GM-CSF were used, and the MSN, OVA and CpG-ODN amounts were controlled. The control MSR-MSN vaccine (V1) described in the previous section, a vaccine with an increased amount of only MSNs (V2), a vaccine with increased amounts of MSNs and an adjuvant (V3), and a vaccine with increased amounts of all three components (V4) were prepared (FIG. 5A). Subsequently, a prophylactic study was carried out using C57BL/6 mice vaccinated with the MSR-MSN vaccines and then inoculated with B16-OVA 7 days after vaccination (FIG. 5B).

Tumor suppression data clearly showed that the number of MSNs and the dose of CpG-ODNs are critical for inducing strong antitumor responses (FIG. 5C). The increase in MSN amount (V2 vaccine) more significantly suppressed tumor growth then V1. In addition, when the CpG-ODN dose was additionally increased compared to V2 (V3 vaccine), the antitumor response was significantly enhanced compared with V2 and V1 (P=0.031 and 0.0015, respectively). The increase of the OVA antigen in the V4 vaccine showed similar levels of antitumor response and survival rate compared with those of the V3 vaccine loaded with a smaller amount of antigen (FIGS. 5C and 5D), indicating that the antigen amount used for V1 is sufficient for initiating an antigen-specific adaptive immune response.

Taken together, these results indicate that a larger amount of MSNs and CpG-ODN loaded at a higher level increase the possibility of the recruited DCs to sense an antigen and a danger signal in the immunogenic microenvironment of the scaffold, resulting in higher vaccine efficacy.

Example 5. Synergistic Effect of Dual-Scale Vaccine and Immune-Checkpoint Blockade-Based Immunotherapy for Melanoma Treatment Finally, a therapeutic effect of the MSR-MSN vaccine was investigated using a tumor model. C57BL/6 mice were first inoculated with $5 \times 10^5$ B16-OVA cells per mouse. The mice were inoculated with the optimized MSR-MSN vaccine (V3) on day 5 after tumor inoculation (FIG. 6A). The MSR-MSN vaccine clearly delayed tumor growth in a prophylactic experiment compared with the untreated control group (FIG. 6B), and thus the survival rate of the animals increased (FIG. 6C). However, in the therapeutic effect experiment, tumor suppression and a survival rate showed limited efficacy compared with those in the prophylactic experiment. This is because various mechanisms block the infiltration of cancer-specific T cells into a tumor, and their activity was suppressed via endogenous ligands within the TME [D. H. Munn et al, Curr. Opin. Immunol. 39 (2016) 1-6].

Immune checkpoint blockade (ICB) therapy, which includes the suppression of programmed cell death protein 1 (PD-1) and cytotoxic T-lymphocyte-associated antigen 4 (CTLA-4) expressed in T cells, and programmed death-ligand 1 (PD-L1) expressed in cancer cells by antibodies, had emerged as one of the most effective methods for treating cancer. The binding between CD80/CD86 on APCs and CD28 on T cells is necessary for T cell activation. However, since CTLA-4 has high avidity and affinity to CD80/CD86, the activation may be inhibited by CTLA-4 expressed on T cells, leading to the inhibition of T cell activation in the early stage, and immune tolerance to a tumor. By blocking CTLA-4 expressed on T cells by an anti-CTLA-4 antibody, the antigen-activated DCs may effectively prime T cells through the CD80/86-CD28 costimulatory interaction.

To further improve therapeutic efficacy, the synergistic effect of the anti-CTLA-4 ICB (a-CTLA-4) and the MSR-MSN vaccine (V3) in a melanoma mouse model was evaluated. After tumor inoculation, the mice were intraperitoneally administered the a-CTLA-4 antibody (100 μg per mouse), and vaccinated with a single MSR-MSN vaccine 6 days after tumor inoculation (FIG. 6D). The MSR-MSN vaccine and a-CTLA-4 were also administered for comparison. Four injections of the CTLA-4 antibody showed tumor suppression in a therapeutic model, which is a similar level to the effect caused by a single injection of the MSR-MSN dual-scale vaccine. In contrast, the combination of ICB therapy and antigen-specific vaccination synergistically increased an anti-tumor response, thereby suppressing tumor growth and increasing the animal survival rate (FIGS. 6E and 6F). These results indicated that the blocking of CTLA-4 on T cells inhibits competitive binding between CTLA-4 and CD80/86 in DCs. As a result, DCs expressing a high level of CD86 induced by the MSR-MSN vaccine may effectively prime naive T cells to generate antigen-specific cytotoxic T cells.

CONCLUSION

The inventors prepared a cancer vaccine-based dual-scale mesoporous silica system that enhances and prolongs the intracellular uptake of the MSN vaccine by a large amount of DCs recruited into the MSR microporous scaffold. The MSR-MSN vaccine promoted the generation of a larger amount of cytotoxic antigen-specific T cells against cancer than the MSN vaccine. In addition, the MSR-MSN vaccine exhibited increased anti-tumor prophylactic efficacy and animal survival rates compared with the MSR vaccine. The increased efficacy of the dual-scale particle-based cancer vaccine was caused by the improvement of the DC uptake of MSNs and the migration of DCs to dLNs over time. This strategy may be used to effectively deliver vaccines in the form of large nanoparticles (>100 nm) to DCs.

The tumor suppression effect of the MSR-MSN vaccine as a therapeutic cancer vaccine significantly improved an animal survival rate in combination with ICB therapy. This effect exhibited that the MSR-MSN platform is a promising cancer vaccine platform that can be used in combination with the ICB antibody. In addition, the dual-scale strategy of the present invention may be used in a DNA or mRNA vaccine by enhancing the antigen presentation of DCs via an endogenous antigen.

It should be understood by those of ordinary skill in the art that the above descriptions of the present invention are exemplary, and the example embodiments disclosed herein can be easily modified into other specific forms without changing the technical spirit or essential features of the present invention. Therefore, it should be interpreted that the example embodiments described above are exemplary in all aspects, and are not limitative.

The invention claimed is:

1. A method of preventing or treating cancer, the method comprising:
   administering a dual-scale porous silica particle-based pharmaceutical composition to a subject in need thereof,
   wherein the composition comprises:
   cancer-antigen- and negatively charged adjuvant-loaded positively charged porous silica nanoparticles, which are physically adsorbed onto surfaces of
   porous silica microparticles carrying a chemoattractant attracting dendritic cells (DCs).

2. The method of claim 1, wherein the porous silica microparticles form a 3D construct with a micro-sized space between the particles by self-assembly in a body, and
   wherein the porous silica nanoparticles are located in the space of the 3D construct.

3. The method of claim 2, wherein immature DCs are recruited into the micro-sized space, and the porous silica nanoparticles are internalized into the recruited DCs.

4. The method of claim 3, wherein the immature DCs in which an uptake of the porous silica nanoparticles occurs mature and migrate to lymph nodes.

5. The method of claim 1, wherein the porous silica nanoparticles are mesoporous silica nanoparticles.

6. The method of claim 1, wherein the porous silica nanoparticles are 30 to 250-nm nanoparticles having a pore size of 3 to 30 nm.

7. The method of claim 1, wherein the positively charged porous silica nanoparticles are amine-modified nanoparticles or charged polymer-adsorbed nanoparticles.

8. The method of claim 1, wherein the antigen or adjuvant is additionally loaded in pores of the porous silica nanoparticle.

9. The method of claim 1, wherein the porous silica microparticles are mesoporous silica microrods.

10. The method of claim 1, wherein the porous silica microparticles have a length of 30 to 120 μm, and a width of 5 to 30 μm.

11. The method of claim 1, wherein the chemoattractant is selected from the group consisting of a granulocyte macrophage-colony stimulating factor (GM-CSF), chemokine (C-C motif) ligand 21 (CCL-21), chemokine (C-C motif) ligand 19 (CCL-19), a FMS-like tyrosine kinase 3 (Flt-3) ligand and a combination thereof.

12. The method of claim 1, wherein the composition has an increased anticancer effect according to the increase in content of porous silica nanoparticles or adjuvants loaded in the porous silica nanoparticles.

13. The method of claim 1, wherein the composition further comprises an immune checkpoint inhibitor.

* * * * *